(12) United States Patent
Müthing et al.

(10) Patent No.: US 7,635,567 B2
(45) Date of Patent: Dec. 22, 2009

(54) METHOD FOR DETERMINATION OF THE RESPONSIVENESS OF AN INDIVIDUAL TO MISTLETOE LECTIN

(75) Inventors: Johannes Müthing, Bielefeld (DE); Jasna Peter-Katalinic, Potsdam (DE); Martin Langer, Karlsruhe (DE); Babette Möckel, Darmstadt (DE); Jürgen Eck, Heppenheim (DE)

(73) Assignee: Viscum AG (DE)

( * ) Notice: Subject to any disclaimer, the term of this patent is extended or adjusted under 35 U.S.C. 154(b) by 648 days.

(21) Appl. No.: 10/499,297

(22) PCT Filed: Dec. 20, 2002

(86) PCT No.: PCT/EP02/14682

§ 371 (c)(1), (2), (4) Date: Feb. 23, 2005

(87) PCT Pub. No.: WO03/054544

PCT Pub. Date: Jul. 3, 2003

(65) Prior Publication Data

US 2005/0221380 A1    Oct. 6, 2005

(30) Foreign Application Priority Data

Dec. 21, 2001 (EP) ................... 01130745

(51) Int. Cl.
*G01N 33/53* (2006.01)
*G01N 33/567* (2006.01)

(52) U.S. Cl. ...................... 435/7.1; 435/7.21

(58) Field of Classification Search .................. None
See application file for complete search history.

(56) References Cited

OTHER PUBLICATIONS

Galanina OE, et al. Journal of Molecular Recognition 10(3):139-147, May 1997.*
Wu AM, Biochemical and Biophysical Research Communications 214(2):396-402, 1995.*
Schwartz-Albiez R, Journal of Biological Regulators and Homeostatic Agents 14(4):286-287, Dec. 2000.*
Muthing J, et al. Biochemistry 43(11), 2996-3007, Mar. 23, 2004.*

\* cited by examiner

*Primary Examiner*—Robert Landsman
(74) *Attorney, Agent, or Firm*—Connolly Bove Lodge & Hutz LLP

(57) ABSTRACT

A method for the determination of the responsiveness of an individual to mistletoe lectin or to (an) mistletoe lectin single chain(s), wherein the expression of a membrane-bound receptor for mistletoe lectin is characteristic of a corresponding responsiveness.

9 Claims, 15 Drawing Sheets

Figure 1

Figure 2:
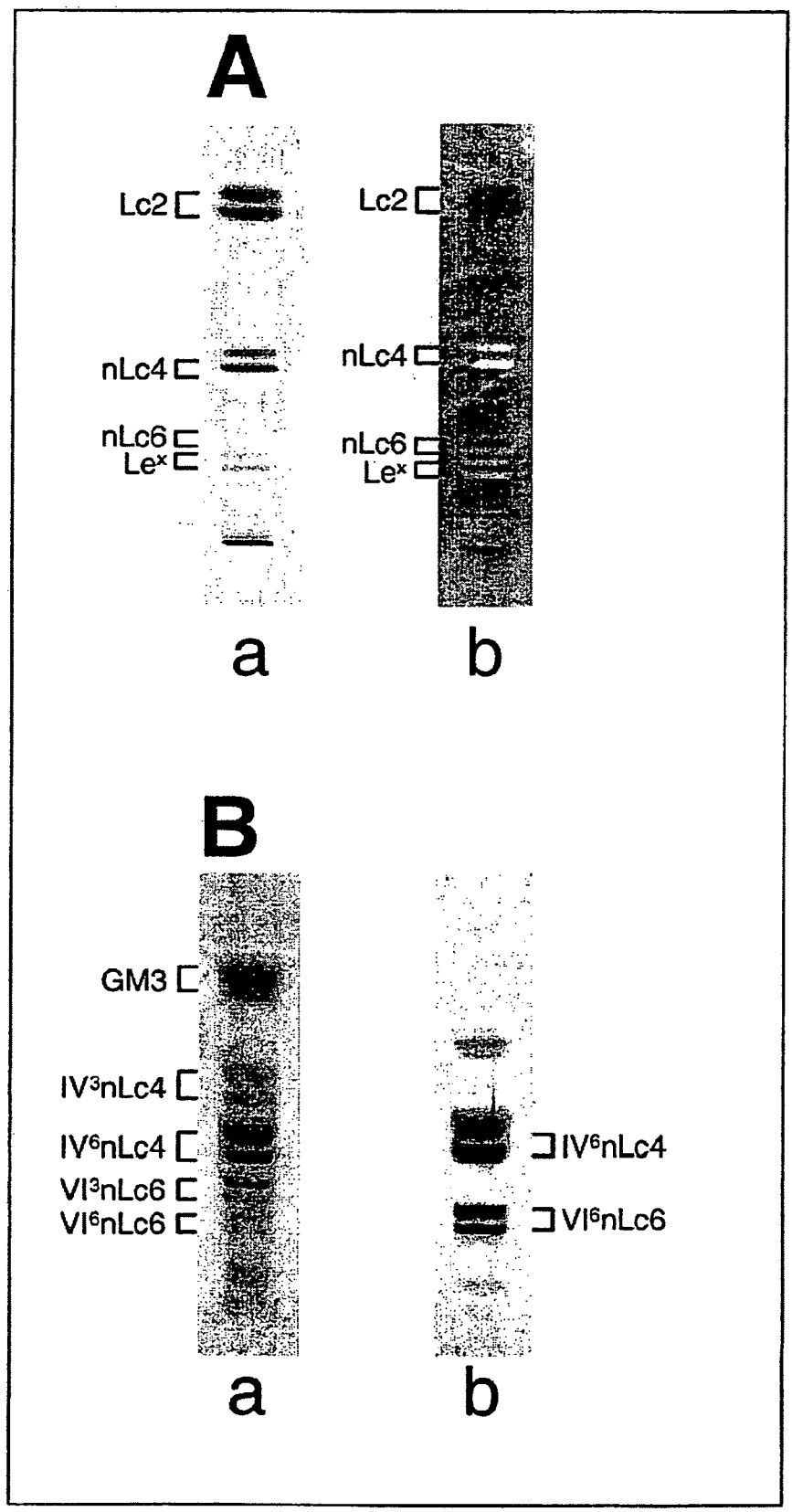

A Neutral glycosphingolipids:

■—●—■—◆—(Cer)

Reaction with rViscumin:

Reaction with ricin: +++++

B Gangliosides:

■—●—■—◆—(Cer)
|
α 6
|
2
Sialic acid

Reaction with rViscumin: +++++

Reaction with ricin:

Figure 6

Test for IgM – Production

Figure 13

|  | rViscumin | ML-I |  |
|---|---|---|---|
| 66 | | | |
| 45 | | | |
| 36 | | | |
| 29 | | | |
| 24 | | | |
| 20 | | | |
| 14 | | | |

M   T     AF    M          AF    T    M

METHOD FOR DETERMINATION OF THE RESPONSIVENESS OF AN INDIVIDUAL TO MISTLETOE LECTIN

RELATED APPLICATIONS

This application is a national stage filing under 35 U.S.C. 371 of International Application PCT/EP02/14682, filed Dec. 20, 2002, which claims priority from European Application No. 01130745.1, filed Dec. 21, 2001, the specifications of each of which are incorporated by reference herein in their entirety. International Application PCT/EP02/14682 was published under PCT Article 21(2) in German.

The present invention relates to a method for determination of the responsiveness of an individual to mistletoe lectin or to a mistletoe lectin single chain wherein the expression of a specific, membrane-bound receptor for mistletoe lectin is characteristic of a corresponding responsiveness.

Various documents are cited in the text of this description. The disclosure content of the cited documents (including all manufacturer's descriptions, instructions, etc.) is herewith incorporated by reference into this description.

Mistletoe lectin is a type II ribosome-inactivating protein (RIP) related to ricin and formed of two protein chains (Barbieri et al., 1993). In this case, the A-chain has an enzymatic rRNA-N-Glycosidase activity, the B-chain has a carbohydrate-binding activity. Recombinant rViscumin provided in *E. coli* is known to the person skilled in the art (EP 0 751 221 B1). In particular, rViscumin produced in *E. coli* is clinically developed as a mono substance. With regard to its primary structure, rViscumin does not exactly correspond to ML-I, ML-II or ML-III that can be found in the mistletoe plant. It is to be assumed that there are, apart from the rVisumin sequence described, further mistletoe lectin variants which are modified by point mutations in the original gene and which can slightly differ in their primary structure. rViscumin could be regarded as a variant of the primary mistletoe lectin and could be understood as a mixture of ML-I, ML-II and ML-III sequences.

The activities of both chains of the misteltoe lectin are necessary for the cytotoxic/cytostatic activity of the protein. In this case, the first step, i.e. the binding of the molecule on the surface of the cell, is of crucial importance.

As in the case of ricin, the mistletoe lectin (and the rViscumin recombinantly produced in *E. coli*; Eck et al., 1999a, Eck et al., 1999b), too, is said to have galactose/lactose specificity (Olsnes et al., 1982; Lee et al., 1992; Gilleron et al., 1998). In this case, the kind of glycosidic linking of the terminal galactose and the subsequent sugar have so far been described as not being important for the specificity of the lectin (Lee et al., 1994; Gupta et al., 1996).

Various mistletoe lectins (ML-I, -II and -III) which differ in their carbohydrate specificity are described in the literature (Franz, 1986). In this case, it is discussed that the specificity of galactose/lactose (ML-I) changes through a mixed form of galactose/lactose and N-acetyl galactosamine (ML-II) to a mistletoe lectin which binds stronger to N-acetyl galactosamine (ML-III). The rViscumin has a galactose/lactose binding activity that is detectable in different ELISA-like methods (Eck et al., 1999b). Other carbohydrate-binding activities of the mistletoe lectins have so far been described very rudimentary only and, in part, in a very contrary manner. Wu et al. (1995a and 1995b); for instance, observed that the capability of ML-I to bind either human α1-acidic glycoprotein or fetuin is reduced significantly if the desialylated counterparts are used. In contrast thereto, said authors found an increase in the binding and a complete precipitation if sialoglycoprotein from rat in desialylated form was used in the test. However, the conclusions drawn by Wu et al. cannot be interpreted due to the contradictory results of the sialic acid carrying or desialylated proteins used. Furthermore, it is to be noted that the glycosylation of the proteins is not uniform. A desialylation process is a chemical process and varies depending on the manufacturer's indications. In a desialylated sample, for instance, there may still be a residue of proteins carrying sialic acid in a terminal position which falsify the results communicated. Nevertheless, a specificity of ML-I to sialic acid was discussed as the authors succeeded in reducing the protein mistletoe lectin interaction if the oligosaccharide Neu5Acα2-3/Neu5Acα2-6Gal-β1-4Glc was used as a competitor. In the tabular summary of the competition results of a precipitation experiment (microprecipitation technique) it is however striking that, if the same test set up was used, a precipitation of ML-I by various glycoproteins (human α-1 acidic glycoprotein; fetuin, asialo RSL) can be prevented by both lactose and the mixture Neu5Acα2-3/Neu5Acα2-6Gal-β1-4Glc and Galβ1-4GlcNAc in about the same concentrations. A specificity of ML-I for sialic acid cannot be clearly seen from these data, also because the results which were obtained with asialo RSL and fetuin carrying sialic acid in a terminal position have the tendency to be absolutely identical.

At about the same time, Debray et al. (1994) was able to show that the affinity of ML-I immobilised on sepharose 4B to either O-3 or O-6 sialylated lactose or sialo-N-glycosyl peptides has slightly increased compared to N-acetyl-lactosamine-type oligosaccharides and glycopeptides. In this case, Debray et al. (1994) used oligosaccharides and glycopeptides which they partly isolated from human sources (e.g. urine, human serum transferrin, human α-1 acidic glycoprotein). Debray et al. carried out examinations on a column to which they immobilised mistletoe lectin I (ML-I sepharose). When assessing the saccharides tested, they differentiated between three factors. Fraction 1 (FNR) showed no interaction with the mistletoe lectin and eluted in PBS in the elution volume of the column. A second fraction (FR) eluted with slight retardation, however still with use of PBS. Accordingly, saccharides of these two fractions differed only slightly with regard to their capability to interact with the lectin immobilised on the column. The actually binding fraction (FE) could only be eluted by 150 mM galactose in PBS buffer. The results are not conclusive. The authors discussed, for example, a retardation of the elution of FNR compared to FR if they linked a sialic acid α2-6 to the terminal galactose residues (cf. saccharides 16 (FR) and 17 (FNR)). However, a double sialic acid labelling, as can be seen in saccharide 15 (FR), did not result in the substance binding more strongly to the ML-I on the column. It is however difficult for the skilled person to discuss explicitly the retardation of FNR compared to FR. Thus, the slight retardation (FR) is likely to be caused by unspecific interactions (e.g. hydrophobic interactions) with the protein bound to the column and is not due to the specificity of the mistletoe lectin. Only two of the structures tested eluted after rinsing the column with PBS buffer+150 mM NaCl+150 mM galactose (FE). These two structures were isolated from bovine thyroglobulin or turtledove ovomucoid. In contrast to all other structures which the authors used and mainly contained the structure Gal(β1-4)GlcNAc-, these structures terminally have two galactose residues which are linked either α1-4 or α1-3 to the second galactose.

Lee et al. (1994) described the relevance of the second sugar residue for the recognition of ML-I. They divided the recognition of sugar structures by ML-I up into four groups and were able to show that GlcNAc structures at the second position greatly impaired the recognition of the sugars. They found, the strongest affinity of ML-I to a saccharide with the terminal sugar residues β-D-Gal-(1-2)-β-D-Gal-. The β1-3-linked galactoses, too, showed similarly good specificities. Lee et al. (1994) did not test β4-linked galactoses, it can however be concluded from the work of Debray et al. (1994) that these, too, should have a high specificity to ML-I.

When assessing the work of Debray et al. (1994), it must however be noted that the examinations were carried out with mistletoe lectin which had been immoblised on a column. The interactions of the saccharides, which were observed, with the immobilised lectin are an unphysiological experimental system. Thus, it is not possible to directly draw a conclusion with regard to the interaction of dissolved mistletoe lectin or rViscumin in solution with a receptor.

The data presented herein by Lee et al. (1994), Debray et al. (1994) and Wu et al. (1995) with regard to the specificity of mistletoe lectin contradict each other and cannot be considered a conclusive evidence of a specificity of the mistletoe lectin to Neu5Ac. It is particularly problematic that the data were not carried under defined test conditions. In particular, this refers to the quality of the proteins used which, for technical reasons, never have a homogeneous carbohydrate structure.

On the basis of the observations by Lee et al. (1992), Galanina et al. (1997) designed an experimental system in which mistletoe lectin was coupled to structurally defined neoglyco-conjugates. In this system, the competitive potency of synthetic oligosaccharides to reverse the binding of mistletoe lectin was examined. Yet, the results obtained with this system are also heterogenous. A competitive potency of lactose was shown as expected. The competition with N-acetyl-lactosamine leads to similar results. Moreover, naturally occurring isomers of the sialyl-lactose were examined, too. In this case, however, the α2-3 sialylated isomer had a higher competitive activity than the α2-6 sialylated isomer, which, however, was clearly below the one of lactose or N-acetyl-lactosamine. Moreover, the authors stated that N-acetyl-neuramic acid alone did not have an inhibitory activity. In the analysis of the works based on competitive studies, it is striking that the naturally occurring glycoproteins examined comprised soluble proteins only. Membrane-bound glycoproteins were not examined in the experiments described.

Mistletoe lectin, but also, for example, other lactose/galactose-specific proteins such as ricin or galectin are described as asialo-fetuin-binding proteins. This property can also be utilised for a quantification (Vang et al., 1986). Gupta et al. (1996) were able to describe the interaction of the proteins ricin, galecting or mistletoe lectin (here designated as *Viscum album* agglutinin) in more detail. They found that all three proteins form defined complexes with asialo-fetuin. The receptor(s) that is (are) responsible for the binding of the mistletoe lectin or ricin to the target cell is (are) not yet known.

In 1982, the receptor for the cholera toxin was identified on Balb/c 3T3 cells (Critchley et al., 1982). It is the ganglioside GM1. Based on this work, it was tried to search for the receptors of other toxins/lectins in this area, too. In this case, for ricin and peanut agglutinin it could be shown that the receptors on human lymphocytes are glycoproteins whereas *Ricinus* agglutinin and, soybean agglutinin bind to glycoproteins and gangliosides to about the same degree (Turpin et al., 1984). In examinations with model membranes in which the monosialo ganglioside GM1 (with terminal galactose) was inserted only very unspecific interactions with the two proteins ricin and mistletoe lectin were observed which did not make it possible to clearly differentiate the permeability of the membranes depending on the type II RIPs added (Pohl et al., 1998a). Furthermore, Pohl et al. (1998b) observed that both ricin and mistletoe lectin were able to induce vesicle-vesicle fusions. The model of fusion induction, however, is not crucially relevant for the uptake of mistletoe lectin or ricin in vivo as membrane fusions are not made responsible for the uptake of these proteins by a target cell. In 1990, Tonevitsky et al., already showed that the ganglioside GM1 could not be regarded as the receptor. Utsumi et al. (1987) reported on a binding of ricin to GM1-containing liposomes, which could not be observed when the competitor lactose was added.

Samal et al. (1995) observed that mistletoe lectin, like ricin, aggregates with blood platelets. According to this analysis, mistletoe lectin does however not aggregate liposomes isolated from blood platelets, said liposomes being aggregated by ricin. The authors did not discuss a potiential receptor for these lectins.

In 1994, it was observed that the changed surface structure of degenerate cells can be utilised (Gottstein et al., 1994; Usui & Hakomori, 1994). Immunotoxins, for example, were suggested for a therapy, said immunotoxins consisting of monoclonal antibodies against specific glycolipid or glycoprotein structures, which are preferably present on the degenerate cells only, and the toxic component of ricin (ricin A-chain) (Goffstein et al., 1994; Usui & Hakomori, 1994). This model emphasises the relevance of a cell-specific vehicle which makes a transport of a toxin into a target cell possible.

In the case of ricin, the carbohydrate-binding B-chain does not fulfil the requirements of such a vehicle as a receptor which has not been clearly identified but which occurs ubiquitously has been described for ricin. This observation explains the side-effects described for treating patients with ricin.

As mistletoe lectin, in contrast to ricin, seems to bind to a receptor which does not occur ubiquitously, the B-chain was suggested as possible vehicle for a transport of fused toxins. Corresponding fusion proteins of the B-chain of the rViscumin having cytotoxic compounds were described in EP application EP 1012256 A1. For an efficient and targeted application of corresponding therapeutic agents, it would thus be desirable to identify the receptor which the B-chain of the mistletoe lectin or the recombinantly produced rViscumin binds to.

The use of mistletoe extracts (extracts of *Viscum album*) as a remedy has already been known for centuries. Ingredients in this case called lectins are identified as active components of these extracts. These lectins are proteins which can recognise very specific carbohydrate structures even in lipid- or protein-bound form and can bind thereto. Mistletoe lectin, which was characterised as class II ribosome-inactivating protein, is pharmacologically effective only thanks to the interaction of its two sub-units. In this case, the B-chain of the mistletoe lectin which has sequence motifs with specific carbohydrate-binding properties, is responsible for the transport of the protein into the target cell. In the target cell, the A-sub-unit then blocks the ribosomal metabolism in the cell by its enzymatic rRNA-N-glycosidase activity and, in this way, triggers a programmed cell death (apoptosis) in said cell.

The mode of action of the mistletoe plant and the extracts obtained therefrom for treating diseases was described in European patent EP 0 602 686 B1. Since the beginning of this century, mistletoe preparations are used in cancer therapy with mixed success (Bocci, 1993; Gabius et al., 1994; Gabius & Gabius, 1994; Ganguly & Das, 1994). Hajto et al. (1989, 1990) were able to show that the therapeutic effects are mediated in particular by so-called mistletoe lectins (viscumins, *Viscum album* agglutinins, VAA). Apart from the cytotoxic effect, it is today in particular an (unspecific) immunostimulation that is discussed, the positive effects of which are utilised for an accompanying therapy and for the follow-up treatment of tumour patients. An improvement of the quality of life of such patients is possibly brought about by the release of endogenous endorphins (Heiny and Beuth, 1994).

Numerous in vitro analyses (Hajto et al., 1990; Männel et al., 1991; Beuth et al., 1993) and in vivo analyses (Hajto, 1986; Hajto et al., 1989, Beuth et al., 1991; Beuth et al., 1992) and clinical studies (Beuth et al., 1992) prove the increased release of inflammatory cytokines (TNF-α, IL-1, IL-6) mediated by the mistletoe lectin and an activation of the cellular components of the immune system (TH-cells, NK-cells).

Today, a 60 kDa-mistletoe lectin protein is regarded as active principle of the mistletoe extracts wherein the protein can be obtained from extracts by means of biochemistry (Franz et al., 1977; Gabius et al., 1992). The ML-protein consists of two covalently S-S-linked sub-units wherein the A-chain of the protein is responsible for an enzymatic inactivation of ribosomes (Endo et al., 1988) and the B-chain of said protein is responsible for the carbohydrat binding. The biological activity is correlated with obtaining the lectin activity of the B-chain (Hajto et al., 1990).

The technical problem underlying the present invention is that it has so far not been possible to make a targeted prediction as to whether a therapy including the administration of rViscumin or similar compounds is suitable for treating a disease or ailment or an individual.

This technical problem has been solved by the embodiments characterised in the claims.

Thus, the present invention relates to an in vitro method for the determination of the responsiveness of an individual to mistletoe lectin or to (a) mistletoe lectin single chain(s), comprising the step of the specific quantitative and/or qualitative detection of a membrane-bound receptor, wherein the receptor is characterised by a terminal N-acetyl neuraminic acid (Neu5Ac) which is linked to a galactose (Gal) by a glycosidic α2-6 bond.

Thus, according to the invention, an in vitro method for the determination of the responsiveness of an individual to mistletoe lectin or for (a) mistletoe single chain is preferably described wherein the responsiveness is mediated by the specific binding of the carbohydrate-binding sub-unit of the mistletoe lectin to a membrane-bound receptor and the receptor is characterised by a terminal N-acetyl-neuraminic acid (Neu5Ac) which is linked to a galactose (Gal) by a glycosidic α2-6 bond. The determination comprises the specific quantitative and/or qualitative detection of said specific glycosylation.

The term "mistletoe lectin" comprises both the natural mistletoe lectins described herein and known to the skilled person and the recombinant mistletoe lectins wherein the aforementioned mistletoe lectin single chain preferably comprises the mistletoe lectin B-chain or (a) fragment(s) thereof.

In connection with the invention, the term "responsiveness" defines the triggering of a reaction of a single cell, a cell population, a cluster of cells, a tissue, an organ or an organism, said reaction favouring the healing of a disease or an ailment. Furthermore, the term "responsiveness" also comprises the sensitivity of an individual cell, a cell population, a cluster of cells, a tissue, an organ or an organism in preventive application of the rViscumin or similar compounds. Accordingly, a responsiveness of corresponding target cells is connected with a positive therapeutic effect or a preventive effect. Preferably, the "responsiveness" comprises the sensitivity of a human cell, cell population, cluster of cells, tissue, organ or a human organism.

The term "specific binding" can, for instance, be characterised by a "key-keyhole principle". The ligand (mistletoe lectin) and the target molecule (membrane-bound receptor) have structures or motifs which specifically fit each other. An example hereof are an antigenic determinant (epitope) which interacts with the antigen binding site of an antibody. Accordingly, a specific binding is in contrast to a more universal, unspecific binding. When the structure of an interaction partner that specifically bind to each other is known, conclusions as to possible preferred structures or special structural elements of a suitable partner interacting therewith can be drawn. The invention provides the specific interaction partner for mistletoe lectin, in particular rViscumin.

The term "carbohydrate-binding sub-unit of the mistletoe lectin" describes the sequence motifs of the B-chain of the mistletoe lectin which specifically bind to the membrane-bound receptor of the mistletoe lectin. These motifs were described by Langer et al. (2000). Like the carbohydrate-binding sub-unit of the ricin, the B-chain of the mistletoe lectin, too, is formed of 2 domains. These domains are again divided into 3 sub-domains each. The domains are designated as 1 and 2, the sub-domains as α, β and γ. For ricin, it is described that every sub-domain is derived from a presumably bacterial carbohydrate binding structure (Rutenber et al. 1987). Due to the high structural identity of the B-chain of the ricin and the mistletoe lectin (62% identity and 70% homology according to Eck et al., 1999), this observation also seems to be applicable to the mistletoe lectin. According to Langer et al. (2000), the different specificity of the carbohydrate-binding sub-unit of the ricin and the mistletoe lectin is due to the differences in the sub-domains. These are, in particular, in the 1α sub-domain the residues D23 and W38, in 1β the residues Y68, Y70, Y75 and F79 and in sub-domain 2γ the residues D235, Y249; for numbering, cf. Eck et al. (1999a).

In connection with the invention, the term "membrane-bound receptor" defines a membrane-bound structure which is characterised by a terminal N-acetyl neuraminic acid (Neu5Ac) which is again linked to a galactose (Gal) via a glycosidic α2-6 bond. Examples of corresponding membrane-bound structures are proteins or peptides anchored to the membrane of a cell. This definition comprises both transmembrane and membrane-associated proteins and peptides. Lipids which are either themselves part of the membrane or which are associated thereto are also examples of such structures. The membrane-bound structure disclosed can be part of both a glycoprotein (glycosylated protein) and a glycolipid.

In this connection, the term "membrane" explicitly comprises all membraneous, cellular lipid double layers. Accordingly, both membranes of the endoplasmatic reticulum (ER), Golgi apparatus, the nuclear envelope, of vesicles and vacuoles and the outer cell membrane.

In the state of the art, proteins are described which are glycosylated with a terminal N-acetyl neuraminic acid (Neu5Ac) which are linked to a galactose (Gal) via a glycosydic α2-6 bound. These glycosylated proteins, however, are soluble proteins/serum proteins (cf., e.g. Hanasaki et al., 1995) which are neither relevant for the pharmacological effects nor the mode of action of mistletoe lectin. In connection with this invention, a glycosylated membrane-bound structure is disclosed for the first time.

The identification of terminal N-acetyl neuraminic acid (Neu5Ac), which is linked to a galactose (Gal) via a glycosidic α2-6 bond, as a specific target structure of the carbohydrate-binding sub-unit of the mistletoe lectin allows a skilled person, either alone or in combination with the teaching of Langer et al. (2000), for instance, to change the carbohydrate-binding sub-unit of the ricin by site-specific mutagenesis. A peptide/protein mutated accordingly could then no longer bind to a ricin-specific target structures but to mistletoe lectin-specific target structures instead.

Figure 9:
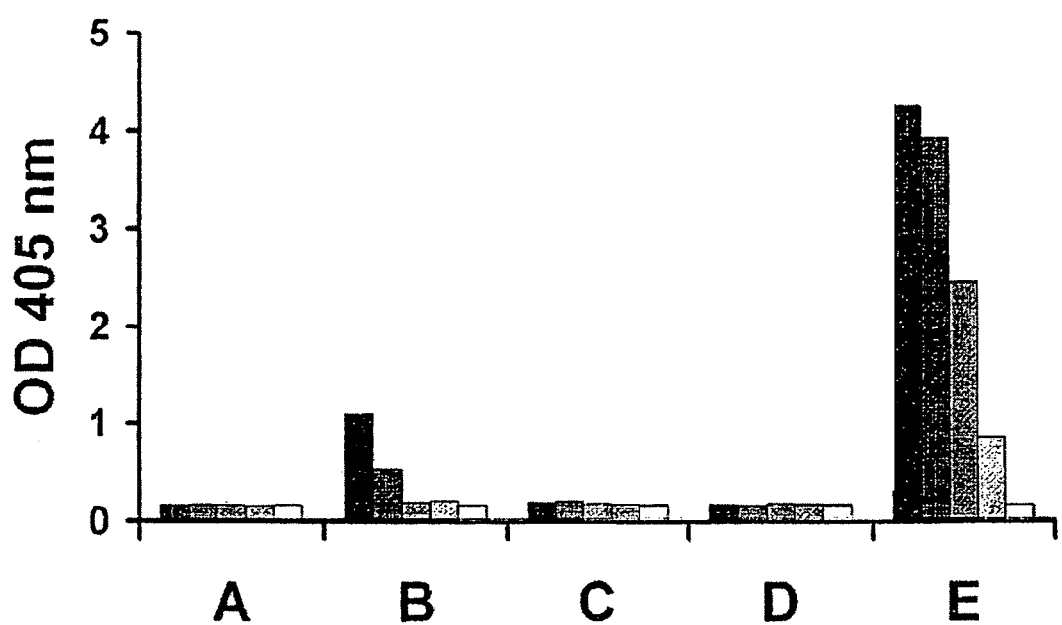

Examples of a quantitative and/or qualitative detection of said glycosylation are known to the person of skill in the art an are described, amongst others, in the enclosed example 7 and in FIG. 9 which illustrates this example. Such methods comprise, for instance, modified Western blot analyses as shown in the examples. Moreover, such methods comprise techniques such as, e.g. the radioimmunoassay (RIA), sandwich (immunometric assay) and Western blot assay, IRMA (immune radioimmunometric assay), EIA (enzyme immunoassay), ELISA (enzyme-linked immunosorbant assay), FIA (fluorescent immunoassay), CLIA (chemiluminescent immunoassay), agglutination assay and flow cytometric methods.

The method of the invention allows, inter alia, a prognosis on the effectiveness of a mistletoe lectin therapy, which includes that a forecast can be made whether a therapy with mistletoe lectin, preferably with rViscumin, can principally be expected to be successful in the treatment of a disease in certain cells, a certain cell population or a certain tissue, organ or organism. If, for example, the aforementioned glycosylation on a tumour cell is identified using the method of the invention, rViscumin can bind to the cell, be absorbed by it and exert a cytotoxic effect in it. Moreover, the method of the invention allows a prognosis of the effectiveness of a mistletoe lectin therapy in an individual. As a consequence, in a group of patients, individual responders (patients responding to the therapy) can be differentiated from non-responders. Such a method of prognosis therefore fulfils a similar task as examinations which the skilled person knows and which are carried out prior to a therapy of breast cancer patients with Herceptin. Before a therapy with the antibody preparation Herceptin is allowed to be administered, it must be tested whether a patient has the EGF-receptor Her-2. In this connection, the FDA (US Food and Drug Administration) has authorised in particular two test methods (immunohistochemistry staining (IHC) and fluorescence in situ hybridisation (FISH)). Cf. in this connection amongst others Thomson et al. (2001). Analogously, such methods and other techniques described herein can be used, according to the teaching of the invention, for recognising and/or determining individual responders to a mistletoe lectin therapy, in particular a therapy with rViscumin.

For the method of the invention, samples of fluids, in particular body fluids, cells, cell populations or tissues can be used. These samples can be derived from blood samples or other samples of body fluids but can also be tissue samples, individual cells or dissaminated tumour cells. Examples of such samples and techniques of how to take them are described in more detail in this application in connection with further embodiments.

The method of the invention also makes it possible to recognise responders in a group of patients early. In this way, it is possible to assess the success of the therapy in a test that can be readily carried out without great delay prior to the beginning of a therapy. This characteristic of the method of the invention is relevant particularly with regard to aspects of disease economy. A possibly cost-intensive therapy which however is ineffective for the individual patient is avoided. In this way, also side effects which are tolerated in the case of an effective therapy if these individual patients for which a successful therapy with rViscumin seems doubtful can be avoided.

As described in the examples, in tests underlying the invention, it could clearly be shown that mistletoe lectin and ricin bind to glycosphingolipids (GSL). It was for the first time possible to document in this case a quantitative and qualitative difference between the binding specificity of mistletoe lectin (in particular rViscumin) and ricin. The carbohydrate structures recognised by the two proteins are schematically shown in FIG. 1.

As is shown in the illustrated examples, it was shown in specific tests that the primary specificity of mistletoe lectin (in particular rViscumin) is not a terminal galactose. FIGS. 2 to 5 and 7 show a modified Western blot/immunologic detection of bound ricin or rViscumin on a DC plate (TLC assay) on which the neutral and acidic GSL have been separated beforehand due to their different running properties in different running agents. While ricin shows a clear specificity for neutral GSL with terminal galactose (Lc2, nLc4, nLc6, Gg4) (table 1; FIG. 4B, lane b), rViscumin surprisingly only shows a very weak binding to Galβ1-4Glcβ1-1Cer (Cer means in this case ceramide) (table 1; FIG. 2A, lane b, negative stain after overnight incubation).

Surprisingly, it was shown that this does however not apply to a group of gangliosides at which an N-acetyl neuramic acid (Neu5Ac) is located terminally which is recognised very well by rViscumin and not at all by ricin (cf, table 1; FIG. 2B, lane b; FIG. 5B, lane b, negative stains). Moreover it was surprisingly found that it is crucial for the recognition of the receptor structure by rViscumin whether the N-acetyl neuramic acid is linked to the terminal galactose of the neutral sugar structure α2-6 (is recognised) or α2-3 (is not recognised) (cf. enclosed examples and figures).

This inventive, specific recognition of N-acetyl neuramic acid in Neu5Ac-α2-6-Gal configuration reminds of the specificity in the epitope recognition of monoclonal antibodies and has not been described so far for misteltoe lectin. The absolutely different specificity of ricin and rViscumin, too, was surprising and not predictable for the skilled person. The different recognition motifs of the two type II-ribosome-inactivating proteins tested are summarised in table 1. It could be concluded from the state of the art that both ricin and mistletoe lectin (in particular rViscumin), if at all, rather bind to the neutral GSL which have a galactose as terminal sugar residue.

In a preferred embodiment of the method, the receptor comprises gangliosides which, after the α2-6-sialylated galactose, at least one N-acetyl glucosamine (GlcNAc), i.e. gangliosides which, after the α2-6-bound N-acetyl neuramic acid to galactose, comprise at least one N-acetyl glucosamine (GlcNAc). As explained below, the following N-acetyl glucosamine (GlcNAc) can however be located both directly and indirectly after the Neu5Acα2-6-Gal structure. Thus, in connection with this invention, it is possible that the method of the invention is based on the (structure) recognition of a ganglioside receptor comprising the structure Neu5Acα2-6-Gal-Y-[GlcNAc]$_x$-Cer. Y can, for instance comprise a further galactose (Gal).

In connection with the invention, the term "ganglioside" defines acidic sialic acid containing ceramide oligosaccharides. The carbohydrate moieties are linked via a glycosidic bond to the C1-OH group of N-acyl sphingosine (=ceramide). Gangliosides can be both long-chain (e.g. IV$^3$nLc4, VI$^3$nLc6, etc.) and branched (GM1 or GM2), (Voet and Voet (1992), in particular the figure on page 271 of this reference).

In a moreover preferred embodiment of the method, the receptor comprises gangliosides with the structure Neu5Acα2-6-Gal-[Gal/GlcNAc]$_x$-Cer wherein Cer is a ceramide. In the method described herein, Neu5Acα2-6-[Galβ1-4GlcNAcβ1-3]$_x$ Galβ1-4Glcβ1-1Cer is particularly preferred.

Common methods for the structural characterisation of gangliosides, at present only allow an exact analysis of gangliosides where x is ≦6. The carbohydrate-binding sub-unit of the mistletoe lectin recognises the terminal sugar structures. Accordingly, the value of the variable x is principally not important for the specific binding. Preferably, the variable has a value of 10 at maximum. Moreover, the variable preferably has a value of ≦6, more preferably a value of 5, 4, 3, 2 or 1. Furthermore, it is preferred that, in the case of branched gangliosides, the value of x is different in individual or all chains.

It is also preferred that, in an embodiment of the method, the receptor comprises gangliosides having the structure Neu5Acα2-6-[Gal1-4GlcNAcβ1-3]$_x$ Galβ1-4Glcβ1-1Cer, the structure Neu5Acα2-6Galβ1-4GlcNAcβ1-3Galβ1-4Glcβ1-1Cer being particularly preferred, or a ganglioside Neu5Acα2-6Galβ1-4GlcNAcoβ1-3Galβ1-4GlcNAcβ1-3Galβ1-4Glcβ1-1Cer.

This preferred embodiment, too, comprises linear and branched gangliosides.

According to a further preferred embodiment, the receptor is cell membrane-bound.

This embodiment of the method of the invention describes the analysis of membrane-bound receptors which form part of the outer cell membrane or are bound thereto. In particular, said embodiment comprises receptors that are glycoproteins or glycolipids.

In a further preferred embodiment, the mistletoe lectin is a recombinant mistletoe lectin/rViscumin.

As described above, in the literature a difference is made between various naturally-occurring mistletoe lectins (ML-I, -II and -III). They differ in their carbohydrate specificity (Franz, 1986). In this case, it is discussed that the specificity of galactose/lactose (ML-I) changes from a mixed form of galactose/lactose and N-acetyl galactosamine (ML-II) to a mistletoe lectin which binds more strongly to N-acetyl galactosamine (ML-III). The skilled person knows recombinant mistletoe lectin/rViscumin provided in *E. coli* (EP 0 751 221 B1; Eck et al., 1999a and 1999b). The primary structure of rViscumin does not exactly correspond to an ML-I, ML-II or ML-III that can be found in the mistletoe plant. It can be assumed that, apart from the rViscumin sequence described, there are other mistletoe lectin variants modified by other site mutations in the original gene, which may slightly differ in their primary structure. rViscumin could be regarded as a variant of the primary mistletoe lectin and could be understood as a mixture of ML-I, ML-II and ML-III sequences.

Moreover, this embodiment comprises recombinant fusion proteins on the basis of the rViscumin as described in EP patent application EP A2 1012256.

Furthermore, it is preferred that, in one embodiment of the invention, the recombinant mistletoe lectin comprises an amino acid sequence which is encoded by a polynucleotide as shown in SEQ ID No.: 1. SEQ ID No.: 3 or SEQ ID No.: 5.

A further preferred embodiment preferably also comprises a recombinant mistletoe lectin encoded by one or more polynucleotides.

In a preferred embodiment of the method of the invention, the recombinant mistletoe lectin also comprises a polypeptide with an amino acid sequence as shown in SEQ ID No.: 2, SEQ ID No.: 4 or SEQ ID No.: 6 or a functional fragment thereof.

In connection with this invention, the term "functional fragment" defines fragments of the polypeptides mentioned which have the same biological function as the polypeptides shown with an amino acid sequence (SEQ ID). The function of mistletoe lectin, in particular rVisumin, and the known sub-units of the mistletoe lectin has already been described herein. The "function" also comprises the specific binding property disclosed herein of the mistletoe lectin, in particular of the B-chain of the mistletoe lectin, for the mistletoe lectin receptor described. Thus, fragments of the mistletoe lectin B-chain, in particular fragment which can mediate a specific interaction with the mistletoe lectin receptor described are comprised, too.

In this context, the term "same biological function" describes for instance that, e.g. fragments or derivatives of the polypeptides induce the same signals in a cell as the peptides mentioned. Examples of fragments are peptide domains with defined functions or specific prosthetic groups. The "same biological function" also comprises the cytotoxicity, immunostimulation (both of the native and the adaptive immune system), stimulation of the release of cytokines, antigenicity, induction of the expression or the activation of surface markers (e.g. CD56 on NK cells), induction of apoptosis or endorphin stimulation.

In a further preferred embodiment, recombinant mistletoe lectin is also comprised which is encoded by one or more polynucleotides which encode a polypeptide with an amino acid sequence as shown in SEQ ID No.: 2, SEQ ID No.: 4 or SEQ ID No.: 6 or a functional fragment thereof, the sequence of which is however degenerate when the genetic code is taken into consideration.

The mistletoe lectin receptor described herein for the first time also plays a role in cellular tests as described in the examples. It could be shown that cells react differently to a treatment with rViscumin. In particular tumour cells or cells derived from tumour cells show, as described in the examples, specific biochemical reactions to the treatment with rViscumin.

By the experiments described in the examples, it was also possible to clearly identify the specificity of rViscumin for the receptor disclosed herein. Moreover, it was clearly shown that rViscumin has a quantitatively different carbohydrate specificity compared to ricin.

In the experiments underlying the invention and described in the examples, it was shown that tumour cells or tumour cell lines express the aforementioned specific receptor for mistletoe lectin, in particular rViscumin.

An alternative embodiment of the method of the invention is an in vitro method for the determination of a responsiveness to mistletoe lectin(s) which comprises the quantitative and/or qualitative determination of the sialyltransferase(s).

Sialyltransferases are responsible for the terminal glycolsylation of glycosylated structures in eukaryotic cells. The activity of these enzymes was found in the Golgi apparatus (in the trans-Golgi compartment). The enzymes catalyse the transfer of sialic acid residues. The enzyme activity of such sialyltransferases catalyses, for instance in degenerate cells (cancer cells), a specific glycosylation of peptides and/or lipids. A presence of such sialyltransferases in cell or tissue samples can be considered an indication of a degeneration of cells. This holds even more true for the detection of an enzymatic activity of these sialyltransferases in a sample.

Methods of molecular biology and protein biochemistry for the quantitative and/or qualitative determination of sialyl transferase(s) are known to the skilled person from the literature (cf. amongst others, Mülhardt (2000) and Rehm (2000)). Methods of molecular biology are for instance RT-PCR techniques, RNAse projection assays, Northern blot or Southern blot analyses. Methods of protein biochemistry are for instance methods for detecting a transferase activity but also methods such as Western blot analysis or other techniques that can be summarised in the term "proteom analysis".

Furthermore, the quantitative determination of the sialyl transferase of individual cells can for example comprise disseminated tumour cells. Individual cell analyses are known to the skilled person and described in EP A1 11009938 and Klein (1999).

An example of a corresponding sialyl transferase is the β-galactoside α-2,6-sialyltransferase E.C. 2.4.99.1 (α2-6STN). α2-6STN is a 47 kDa-transmembrane protein. Hepatocytes also secrete a 41 kDA-form of said enzyme. Soluble α2-6STN is a serum glycoprotein which is assigned to the group of acute phase reactants and plays a role in pathologic processes (enhanced activity in many carcinomas, e.g. colon carcinoma and cervical carcinoma). The amino acid sequences of the known forms of the enzyme and the nucleotide sequences encoding them are known to the person of skill in the art (cf. accession numbers L29554 (*Rattus norvegicus*), X75558 (*Gallus gallus*), NM_003032 (*Homo sapiens*) and NM_009175 (*Mus musculus*)).

The methods according to the invention, which are presented herein, can be carried out using a specific detection reagent. Such specific detection reagents are capable of interacting with or binding to the mistletoe lectin receptor described herein. Said interaction or binding can be direct or indirect, should however be specific for the receptor described herein. Particularly preferred reagents herein are specific antibodies, antibody fragments or antibody derivatives, aptamers, carbohydrate-binding molecules (e.g. peptides and/or proteins) wherein the reagent has to be capable of recognising and/or binding the mistletoe lectin receptor described herein or its specific components (e.g. the terminal N-acetyl neuramic acid defined herein and linked to a galactose via a glycosidic alpha2-6 bond). Preferably, these detection reagents are labelled wherein the label can comprise radioactive substances, fluorescence dyes, biotin-(strept)avidin, luciferases, CAT, beta-galactosidase, alkaline phosphatase(s), peroxidase(s), further enzymatic labels, digitonin, dyes in general, etc. The method of the invention can however also be carried out by means of an indirect detection of the receptor described herein. Detections of the receptor are illustrated in the examples and can, as mentioned above, also comprise methods such as RIA, ELISA, CLIA, FIA, ELLA, TLC tests, histological methods, direct and indirect (immuno) fluorescence methods or flow-through methods (e.g. FACS analyses, flow cytometry, BIAcore).

In an alternative embodiment, the invention relates to a diagnostic composition comprising a substance which specifically recognises or binds to an aforementioned receptor, preferably selected from the group of antibodies, antibody derivatives, antibody fragments, aptamers and carbohydrate-binding peptides or proteins. According to the invention, however, also lectins, e.g. labelled lectins, could be used for diagnostic purposes. In this case, in particular, labelled lectins are used which are capable of specifically binding to the receptor described herein.

Methods for producing antibodies (polyclonal or monoclonal) which recognise or bind a specific target structure are known to the skilled person. The production of monoclonal antibodies against the gangliosides GD1 and GD2, which play a role in neurological diseases, was described by Magnani et al. (1982), Tur et al. (2001) and Pan et al. (2001). The detection of the specificity of such antibodies can, amongst others, can [ . . . ][1] by overlay assay which is based on an immune staining after thin-layer chromatography (Müthing and Mühlradt (1988), Müthing and Kemminer (1996), Müthing (1998)). Said method can optionally also be combined with ELISA.

[1] translator's note: verb missing in the original

The antibodies to be used in the method described herein are preferred to be monoclonal antibodies (or fragments or derivatives thereof) which specifically bind to the membrane-bound receptor structure disclosed herein. In the examples, it is shown how to obtain such antibodies. For example the antibodies described in the examples designated 59.33.3, 59.33.5 and 59.33.6 are directed against the α2-6 sialylated neolacto-type-ganglioside described herein, i.e. the receptor for (recombinant) mistletoe lectin described herein.

The antibodies can, amongst others, be antibodies of the type IgG, IgA, IgD, IgM. A particularly preferred antibody can be obtained from an hybridoma/hybridoma cell line which was deposited with the Deutsche Sammlung von Mikroorganismen und Zeilkulturen GmbH (DSMZ) in Brunswick on 20 Dec. 2002 under the designation 59.33.3 under the accession number ACC2580 according to the Budapest Treaty.

It is also provided for that the diagnostic and pharmaceutical compositions described herein (see below) comprise antibodies which are obtained from the antibodies described herein by modifications of the same. In this way, by means of techniques known to the skilled person, the CDR (complementarity-determining regions; the three complementarity-determining regions CDR1, CDR2 and CDR3 are loops at the end of a V-domain of antibodies or T-cell receptors. They get into direct contact with an antigen or a peptide: MHC complex) of the antibodies described herein can be isolated and said CDR can be inserted in antibodies having a different structure. Thus, it is possible to isolate the CDR from the 59.33.3 antibody (an IgM) and to integrate this CDR in other immunoglobulins, e.g. an IgG, preferably in an IgG1 structure. These methods (e.g. CDR-grafting) are well known to the skilled person. Therefore, the antibodies described herein also comprise chimeric antibodies, humanised antibodies or single-chain antibodies or single-chain antibody fragments such as scFv constructs. However, such antibody modifications are not limited to modifications of the antibodies 59.33.3, 59.33.5 or 59.33.6 described in detail herein. Antibodies to be used can be all antibodies/antibody molecules, antibody fragments or antibody derivatives which specifically bind to the receptor described herein for (recombinant) mistletoe lectin ((r)Viscumin).

Antibody fragments such as Fv, F(ab')$_2$ and Fab can be produced by cleaving the intact protein (antibody), e.g. by protease or by chemical cleavage. A truncated gene may, however, also be designed. A chimeric gene, for instance, which encodes a part of the F(ab')$_2$ fragment comprises DNA sequences which encode the CH1 domain and hinge region of the H-chain followed by a translational stop codon, which results in a truncated molecule.

The term "antibody derivatives" describes modified forms of the aforementioned antibodies. These modifications comprise chemical, in particular biochemical modifications, preferably modifications of protein biochemistry, of the antibodies or their fragments. In this case, the common feature which characterises the antibodies, antibody fragments and their derivatives is the recognition of and/or binding to a specific target structure. According to the invention, said target structure is the membrane-bound receptor for mistletoe lectin described herein. Aptamers and their specific properties have been described as a summary, amongst others, by Hermann and Patel (2000). The skilled person knows methods for isolating aptamers from the state of the art, too.

Herein, the term "carbohydrate-binding peptides" is defined as in the embodiment of the invention which relates to a use for producing a pharmaceutical composition.

In a further preferred embodiment of the diagnostic composition, the substance is detectably labelled.

Examples of detectable labellings of substances are known to the person of skill in the art. They include, amongst others, radioactive, enzymatic or fluorescent labels. Biotinylation and a detection using avidin or streptavidin is also an example of a corresponding preferred embodiment.

An embodiment of the invention comprises the use of the diagnostic composition according to the invention for analysing whether individual cells, a cell population or a union of cells, cells in a tissue, organ or organism have a functional receptor for mistletoe lectin.

In a further alternative embodiment, the invention also relates to the use of an above-defined substance for the preparation of a diagnostic agent for detecting a functional mistletoe lectin receptor.

The use according to the invention of the diagnostic agent for the detection of the receptor which is described herein and which is examined in the examples is moreover preferred on cells.

As shown in the examples, tumour cells which express terminal N-acetyl neuraminic acids (Neu5Ac), which are linked to galactose (Gal) via a glycosidic α2-6 bond, are particularly suitable as responders to mistletoe lectin, particularly to recombinantly produced mistletoe lectin (rViscum).

In a preferred embodiment the examined cells are tumour cells.

More preferred these tumour cells are animal cells, preferably tumour cells derived from mammals, furthermore preferred tumour cells derived from humans. Furthermore preferred these cells are leukaemic cells, microcellular or non-microcellular lung carcinomas, colon carcinomas, CNS carcinomas, melanoma, ovarian carcinomas, kidney carcinomas, prostate carcinomas, mamma carcinomas, bladder carcinomas, gastric carcinomas, pancreatic carcinomas or carcinomas of the testicle.

In a further preferred embodiment of the invention the cells are derived from biopsy material.

Methods for the recovery of biopsy material are known to the skilled person. This description comprises different recovery types, where cells are taken from a proband or patient. Cells which are living cells are preferred. These are for example biopsies carried out with fine needles (fine needle aspirations), punch biopsies, the removal of solid tissue parts (e.g. by surgical methods) or samples of entire organs (e.g. adrenal glands). The different removal techniques are e.g. described in: Kremer et al (1999), Pichlmayr and Löhlein (1991), Niethard and Pfeil (1997), Malte (1998) and Bonk.

In an also preferred embodiment the cells are isolated from blood samples.

Apart from the isolation of cells from blood samples, also preferred embodiments of the invention refer to the isolation of cells from pleural effusions, ascites samples, rinsing fluids, urine samples, sperm samples or samples from spinal and cerebral fluids.

In order to determine the responsiveness of e.g. cancer patients to rViscumin, before a planned therapy or during the course of the therapy, tissue is taken from the patients. It is also possible to take recourse to collected samples/preserved samples of (different) patients (which are stored in many hospitals in paraffin block banks which are arranged according to the indications) in order to be in a position to make a statement with respect to a specific indication which has a sound statistic basis.

These tissues are e.g. lyophilised, preserved in formaldehyde solution or obtained by cryoconservation (purposeful freezing, e.g. after persution with a cytoprotective solution, e.g. sugar solution) and are subsequently further processed according to methods known to the skilled person, e.g. preserved in paraffin blocks. Starting from the samples, slices are prepared which are suitable for an examination with a microscope. Subsequently, these slices are then examined with methods which are well-known to the skilled person (e.g. the LSAP method, a method similar to ELISA or by using the ENVISION method of DAKO in Hamburg) for the presence of the specific antigens, i.e. of the receptor for (recombinant) mistletoe lectin defined herein. To this avail, e.g. samples from patients can be used by using the mAb 59.33.3 or the two other mAbs 59.33.5 or 59.33.6 which specifically recognise the epitope "CD75s" of the receptor described herein. Bound antibodies which can e.g. be used in a concentration of 500 ng/ml up to 10 µg/ml, are then detected with secondary antibodies or other detection methoAan anti-mouse IgM antibody to which polydextrane is linked which is provided with alkaline phosphatase can, e.g, be used. Thus, a comparison between healthy and degenerate tissue is possible as well as a differentiation whether in the case of a patient or in the case of a specific tumour indication a treatment with rViscumin is promising. Moreover, it can be detected whether a treatment with (recombinant) mistletoe lectin ((r)Viscumin) is successful, i.e. the course of the therapy can be monitored.

Moreover, the invention described herein makes other diagnostic methods such as, inter alia, the examination of fine needle biopsy material and xenograft cell lines or other cell lines possible.

The cells can, e.g., be fixed in 96-well plates and can be examined for the presence of membrane-bound/membrane-stable CD75s motifs (rViscumin-binding motifs, i.e of the membrane-bound receptor structure described herein) in a method similar to ELISA, as described in example 8. Another method which can be used for the examination is the FACS analysis. Here, cells can be taken from a pool of cells (interesting particularly in the case of fine needle biopsies) which carry a certain surface antigen. Thus, the cells are at first, e.g., used by using specific antibodies or antibody derivatives such as the mAbs 59.33.3, 59.33.5 or 59.33.6 described herein. Bound antibodies which can preferably, but not excludingly, be used in a concentration of 500 ng/ml to 10 µg/ml, are then placed in an automatic Cell Sorter e.g. by Becton Dickinson together with a secondary antibody, e.g. an anti-mouse IgM antibody which is (fluorescence-) labelled with FITC or otherwise. In this method, in order to filter a specific cell population, a second epitope present on the target cells can be marked with an antibody which is different from the (fluorescence-) labelled anti-mouse IgM antibody and thus only the cells which are in this case labelled twice can be specifically selected. This provides other possibilities to predict the patient with respect to a treatment with rViscumin. Additionally, the information how many percent of a corresponding cell population (cells stained twice vs. cells who are only stained with the second antibody) carry the desired CD75s epitope can be obtained. From such an analysis it can be assessed or taken whether a minimal residual disease exists. Additionally, combination therapies with other anti-tumour agents together with rViscumin can be tested in vitro and can be prepared for the application to a patient.

The diagnostic method as described herein does, however, also comprise the analysis of lysed membrane structures. It is, inter alia, possible to e.g. treat fresh, unfixed biopsy material with detergents (e.g. Triton X-100®, Triton X-112®, Tween 80®, Tween 20®, Octylglycosid, etc.) and to analyse the lysate e.g. by Western blotting or in the form of an ELISA/RIA test. This means that the detergent lysates can be tested for the original presence of the herein described membrane-bound receptor for (recombinant) mistletoe lectin ((r)Viscumin). The skilled person has sufficient methods for the corresponding analysis.

In a further alternative embodiment, the invention refers to the use of a substance which specifically binds to or recognises one of the receptors defined above for the preparation of a pharmaceutical composition for the treatment of proliferative diseases (e.g. cancer), viral diseases (e.g. herpes, HIV), autoimmune diseases or neuronal diseases wherein the receptor-binding or receptor-recognising substance is selected from the group of antibodies, antibody derivatives, antibody fragments, aptamers, low-molecular substances and carbohydrate-binding peptides. Preferably, the receptor-binding or receptor recognising substance is capable to inhibit or weaken a binding of the B-chain of mistletoe lectin and/or rViscumin to this receptor.

In the context of the invention, the term "inhibit" describes a complete as well as a partial inhibition. Thus, the term comprises a total blocking of the binding of mistletoe lectin and/or rViscumin to the carbohydrate structure which has been identified as specific receptor. Moreover, the ability to weaken the binding of mistletoe lectin and/or rViscumin to the receptor is also comprised.

The substance described above for the preparation of a pharmaceutical composition is not mistletoe lectin and particularly not the B-chain of mistletoe lectin.

This embodiment of the invention moreover preferably refers to the formulation of pharmaceutical compositions, possibly in combination with a "pharmacologically acceptable carrier" and/or a diluent. Examples of particularly suitable pharmacologically acceptable carriers are known to the skilled person and comprise buffered saline, water, emulsions such as e.g. oil-in-water emulsions, different kinds of detergents, sterile solutions, etc. Pharmaceutical compositions comprising such carriers can be formulated with the help of known conventional methods. These pharmaceutical compositions can be administered to an individual in a suitable dose. The administration can be carried out orally or parenterally, e.g. intravenously, intraperitoneally, subcutaneously, intramuscularly, locally, intranasally, intrabronchially or intradermally or via a catheter at a site in an artery. The type of dosage is determined by the physician in charge depending on the clinical factors. The skilled person knows that the type of dosage depends on different factors such as e.g. height or weight, body surface, age, sex or the general condition of the patient, but also on the substance which is to be specially administered, the duration and type of administration and on other medicaments which are possibly adiminstered at the same time. A typical dose can e.g. be in the range of between 0.001 and 1,000 µg, with doses below or above of this exemplary range are thinkable, especially when taking the above-identified factors into consideration. Generally, in the case of a regular administration of the composition of the invention, the dose should be in the range between 10 ng and 10 mg units per day or per application interval. If the composition is administered intravenously, the dose should be in a range of between 1 ng and 0.1 mg units per kg body weight per minute.

The compositon can be administered locally or systemically. Preparations for a parenteral administration comprise sterile aqueous or non-aqueous solutions, suspensions and emulsions. Examples of non-aqueous diluents are propyleneglycol, polyethlenegylcol, plant oils such as e.g. olive oil, and organic ester compositions such as e.g. ethyloleate, which are suitable for injections. Aqueous carriers comprise water, alcoholic-aqueous solutions, emulsions, suspensions, salines and buffered media. Parenteral carriers comprise sodium chloride solutions, Ringers dextrose, dextrose and sodium chloride, Ringer's lactate and bound oils. Intravenous carriers comprise e.g. supplements for fluids, nutrients and electrolytes (such as e.g. those which are based on Ringer's dextrose). The composition of the invention can moreover comprise preservatives and other additives such as e.g. anti-microbial compounds, antioxidants, chelating agents and inert gases. Moreover, dependent on the intended use, compounds such as e.g. interleukins, growth factors, differentiating factors, interferons, chemotaktic proteins or an unspecific immunomodulatory agent can be contained. It is particularly preferred that cytostatics, antibiotics and combinations thereof can be contained. The pharmaceutical compositions or medicinal products produced can be used either for the prophylaxis or the treatment of one of the ailments or one of the diseases mentioned above.

The production and methods for the isolation of antibodies, antibody fragments, antibody derivatives and aptamers are known to the skilled person from the prior art as described above and have already been described in more detail above. According to the invention, substances which correspond to a B-chain of the mistletoe lectin or rViscumin or derivatives thereof are not comprised in the group of lectins and carbohydrate-binding peptides. However, this embodiments comprises, inter alia, other lectins which have been adapted with respect to their binding properties to the binding properties of the B-chain for the receptor described herein by biochemical modifications and/or modifications of molecular biology (e.g. directed mutagenesis).

Moreover, in another preferred embodiment, the receptor-binding and/or receptor-recognising substance is linked to a compound with a radioactive, cytotoxic or cytostatic effect.

In this embodiment, the type of link of the substance to a compound with a radioactive, cytotoxic or cytostatic effect depends on the substance and the compound. Preferably, both are, e.g., peptides or proteins. In this case, the linking is preferably carried out by one or more peptidic bonds and/or disulfide bonds. Monoclonal antibodies (mAb) or cytokines which are labelled with radioactive substances are examples of radioimmune substances. A preferred embodiment moreover refers to linking corresponding substances with lectines, toxins or toxoids, preferably from bacteria (e.g. tetanus toxoid, tetanus toxin, diphtheria toxin, cholera toxin, *Pseudomonas* exotoxin, *Pseudomonas* toxoid, pertussis toxin, pertussis toxoid, clostridium exotoxin or clostridium toxoid or from plants (type I RIPs such as saporine or gelonine or type II RIPs such as ricin or the A-chain of type II RIPs or an A-chain of the type I RIPs which is homologous to the type II RIPs). Moreover, other low-molecular molecules with a radioactive, cytotoxic or cytostatic effect (small molecules) and other macromolecules than the ones described above are also comprised.

The term "macromolecules" refers to molecules with a high molecular complexity or a high molecular weight. These are, preferably, biomolecules, such as e.g. biopolymers, particularly proteins, oligo- or polypeptides but also DNA, RNA, oligo or polynucleotides, prosthetic groups, lipids, oligo and polysaccharides and their modifications and also synthetic molecules. The proteins preferably also comprise fusion proteins. The term peptides or proteins comprises natural and synthestic peptides or proteins. Examples of natural proteins comprise inter alia antibodies, antibody fragments, receptors which bind to their specific ligands, peptidic ligands which interact with their specific receptors or peptide domains which interact with specific substrates including proteins and coenzymes and other peptides or enzymes, etc. Moreover, recombinantly produced forms of the proteins or peptides mentioned above are also comprised here. Correspondingly, natural peptides comprise inter alia fragments of the proteins described above which interact with specific affinity ligands. Synthetic proteins or peptides comprise pseudogenes which were brought to expression or fragments thereof and proteins or peptides with a random amino acid sequence.

The term "low-molecular molecules" refers to molecules which have a lower molecular complexity than the macromolecules defined above. In the literature the term "small molecules" or "low molecular weight molecules" is not used consistently. In WO 89/03041 and WO 89/03042 molecules with molecular weights up to 7,000 g/mol are described as small molecules. Commonly, however, molecular weights of between 50 and 3,000 g/mol, more commonly, however between 75 and 2,000 g/mol and mostly in the range of between 100 and 1,000 g/mol are indicated. The skilled person knows examples from the documents WO 86/02736, WO 97/31269, U.S. Pat. No. 5,928,868, U.S. Pat. No. 5,242,902, U.S. Pat. No. 5,468,651, U.S. Pat. No. 5,547,853, U.S. Pat. No. 5,616,562, U.S. Pat. No. 5,641,690, U.S. Pat. No. 4,956,303 and U.S. Pat. No. 5,928,643. Oligomeres or also small organic molecules such as oligopeptides, oligonucleotides, carbohydrates (glycosides), isoprenoids or lipid structures can be indicated as examples of such small molecules. In the literature mostly the molecular weight is the basis for the definition of such small molecules.

In another preferred embodiment of the invention, the compound described above which is linked to the receptor-binding and/or receptor-recognising substance is a peptide.

In a moreover preferred embodiment of the use according to the invention, the receptor-binding and/or receptor-recognising substance comprises a further domain which can induce an immunologic effector function.

In the context of the invention, the term "immunologic effector function" describes inter alia effector functions of the immune system which lead to the eleimination of the cell which carries the receptor (target cell). The elimination is preferably an induction of programmed cell death (apoptosis), but optionally also a nectoric elimination of target cells. In vitro methods for the detection of cell death are known to the skilled person (cf. inter alia Dulat et al. (2001)).

The induction of such immunologic effector functions is preferably the induction of a signal which labels the target cell for the immune system of the organism. Preferably, the target cell is only recognised by the immune system due to this induction. It is moreover preferred that due to this induction, the cell is better recognised by the immune system. The therapy of the target cell is made possible by the recognition or better recognition of the target cell by the immune system.

In a preferred embodiment, the induced immunologic effector function is a cellular effector function.

Examples of cell-mediated immunologic effector functions are the elimination of target cells by effector-T-cells, monocytes or macrophages.

Particularly, MHC-mediated and $F_c$-receptor-mediated effector functions are comprised by the cellular effector function.

In an alternative preferred embodiment, the induced immunologic effector function is a humoral effector function.

Examples of humoral effector functions of the immune system are antibody-mediated reactions or reactions of the complement system. In this connection, the induction of an opsonization of target cells is a preferred embodiment of the invention.

The figures show:

FIGS. 1A and 1B: Potential structures of different receptors of rViscumin and ricin (schematically)

Schematic representation of the receptors of ricin (FIG. 1A) and rViscumin (FIG. 1B). The representation results from the interpretation of the results of the TLC overlay assay summarised in FIGS. 2 and 3 and FIGS. 4 and 5. Gal=galactose, GlcNAc=N-acetyl-glucosamine, Glc=glucose, Cer=ceramide, Sialic=sialic acid. The receptors of rViscumin are gangliosides with terminal α2-6 linked sialic acid residues. The recognition of structures which have been recognised by ricin (FIG. 1A) is not carried out by rViscumin.

FIGS. 2A and 2B: TLC test for the identification of gangliosides, which are specific for rViscumin, in different cell fractions TLC overlay binding tests of rViscumin with neutral GSL (A) and gangliosides (B) of human granulocytes. (A) Lane a: Chromatogram of 15 μg neutral GSL (stained with Orcinol, complete sugar staining); lane b: corresponding overlay assay. (B) Lane a: Chromatogram of 15 μg human gangliosides from human granulocytes (stained with resorcinol, sialic acid staining); lane b: corresponding overlay assay.

FIGS. 3A, 3B and 3C: TLC test for to specification of the binding specificity of rViscumin to carbohydrate on isolated gangliosides (A) Resorcinol staining (example 1); (B) anti-IV$^6$nLc4Cer antiserum TLC overlay test (example 1); (C) rViscumin TLC overlay test (example 2): all TLC assays were carried out with HPLC-purified α2-3- and α2-6-sialylated neolacto series monosialogangliosides. The application is identical in all three chromatograms: lanes a: 15 μg human brain gangliosides (HBG); lanes b: 15 μg human granulocyte gangliosides (HGG); lanes c: 4 μg IV$^3$nLc4Cer (HGG1); lanes d: 4 μg VI$^3$nLc6Cer (HGG2); lanes e: 4 μg IV$^6$nLc4Cer (HGG3); lanes f: 8 μg VI$^6$nLc6Cer and IV$^6$nLc4Cer.

FIGS. 4A and 4B: TLC test forte identification of binding motifs which are specific for ricin (A) Orcinol staining and (B) ricin TLC overlay test with neutral GSL. The application is identical in both chromatograms. Lanes a: 10 μg neutral GSL from human erythrocytes: lanes b: 15 μg neutral GSL from human granulocytes; lanes c: 20 μg neutral GSL from MDAY-D2 cells.

FIGS. 5A and 5B: TLC test with ricin on ganglioside binding (A) Orcinol staining and (B) ricin TLC overlay test gangliosides. Lanes a: 10 μg human brain gangliosides (HBG); lanes b: 8 μg human granulocyte gangliosides (HGG).

Figure 6:
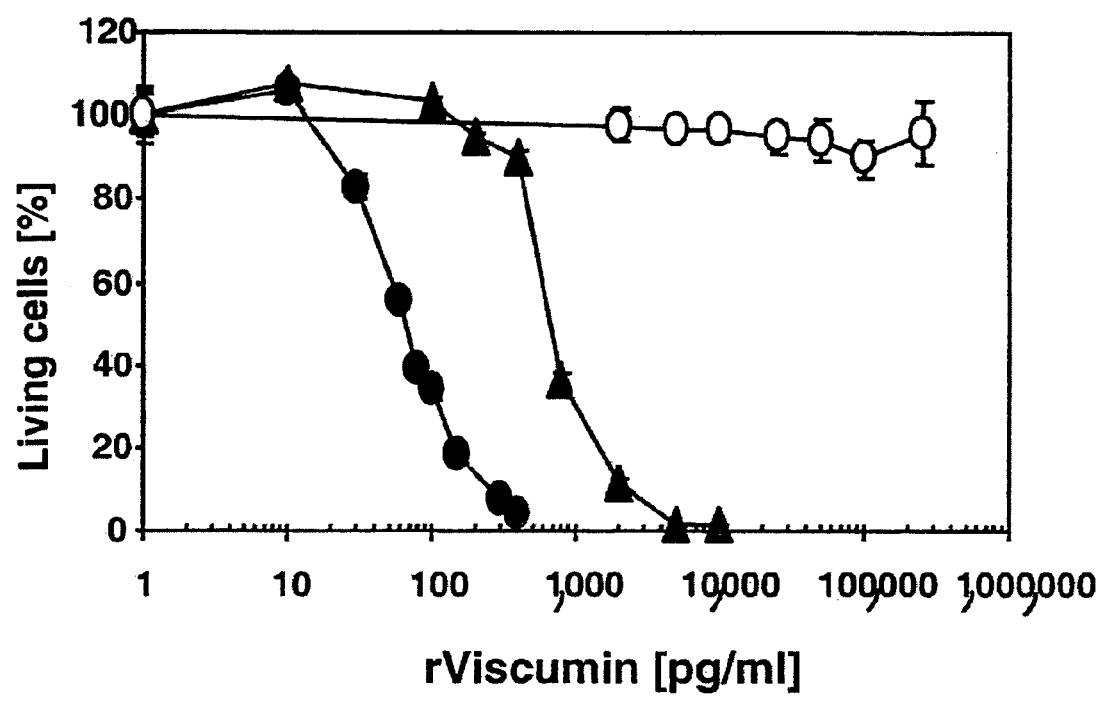

FIG. 6: Cytotoxicity test with different sensitive cell lines

Description of the biologic activity of rViscumin: viability of HL-60 cells (points), 5637-cells (triangle) and CHO-K1 cells (open circles) were applied against the rViscumin concentration. Viability was measured by means of colorimetric reaction of WST-1 and depicted as % living cells compared to an untreated control. The half-maximal cytotoxicity which corresponds to the turning point of the curve was taken as measurable variable. These $IC_{50}$ values were calculated for HL-60 for 66 pg/ml and for 5637-cells for 690 pg/ml. The CHO-K1 cells are to be considered insensitive vis-à-vis rViscumin up to an applied measured rViscumin concentration of 300 ng/ml.

FIGS. 7A and 7B: Semiquantitative correlation of the sensitivity against rViscumin with the occurrence of a ganglioside band which is specific for rViscumin (A) Orcinol staining and (B) anti IV$^6$nLc4Cer antiserum TLC overlay test with gangliosides from in vitro propagated cell lines.

(A) Lane a: 7 μg human granulocyte gangliosides (HGG); lane b: gangliosides from 1×10$^7$ CHO-K1 cells; lane c: gangliosides from 4×10⁷ 5637-cells; lane d: gangliosides from 4×10⁷ HL-60 cells; lane e: 10 μg human brain glangliosides (HBG).

(B) Lane a: 0.134 μg human granulocytes gangliosides (HGG); lane b: gangliosides from 1×10⁷ CHO-K1 cells; lane c: gangliosides from 1×10⁷ 5637-cells; lane d: gangliosides from 1×10⁷ HL-60 cells; lane e: 10 μg human brain gangliosides (HBG). Lane a shows both positive controls IV⁶nLc4Cer (C24 fatty acid, substance 1) and IV⁶nLc4Cer (C16 fatty acid, substance 2) for the identification of specific gangliosides of the neo-lacto series.

Figure 8:
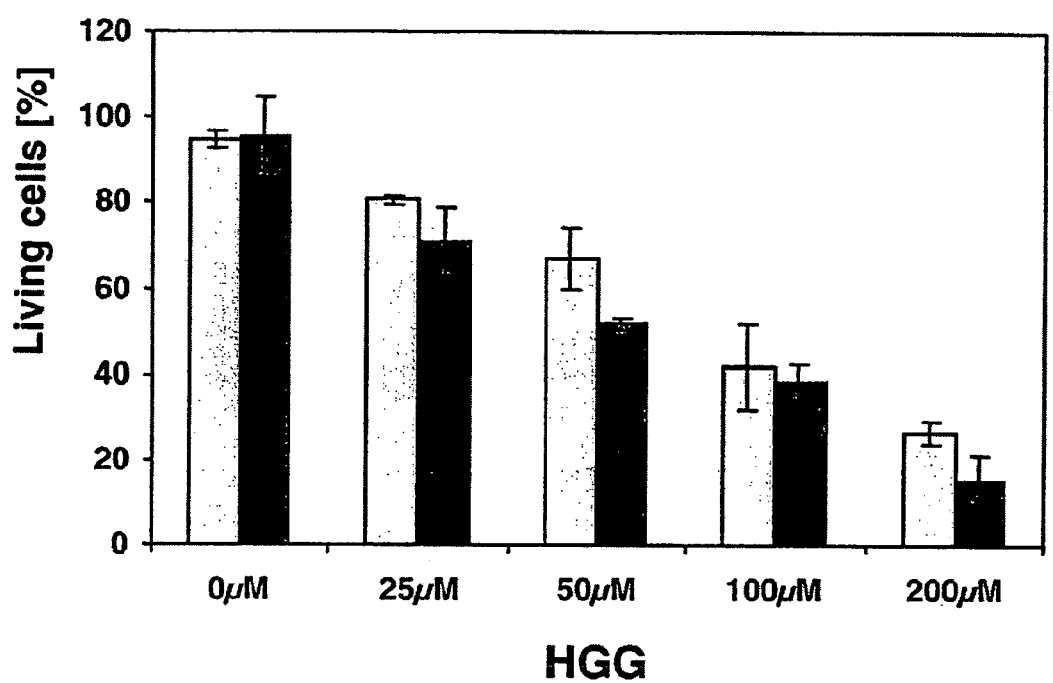

FIG. 8: Sensibilisation vis-à-vis the cell line CHO-K1 which is insensitive to rViscumin by preincubation with specific gangliosides.

Increasing amounts of human granulocyte gangliosides were placed into wells where CHO-K1 cells grow and were incubated there for 48. The cells were washed either with serum-free medium (light gray bands) or with serum-containing medium (dark bands) and were subsequently treated with 300 ng/ml rViscumin for another 48 hours. The viability was measured with WST-1 and was depticted as % to the untreated control (not with gangliosides and rViscumin).

FIG. 9: Enzyme-linked lectin assay (ELLA) of rViscumin with neutral GSL and gangliosides which are adsorbed to the microtiter plate Quantities of GSL from different sources correspond to the bands from the left to the right:
A) Neutral GSL from human erythrocytes: 10, 5, 2.5, 1.25 and 0 μg
B) Neutral GSL from human granulocytes: 15, 7.5, 3.75, 1.9 and 0 μg
C) Neutral GSL from MDAY-D2 cells: 20, 10, 5, 2.5 and 0 μg
D) Human brain gangliosides (HBG): 10, 5, 2.5, 1.25 and 0 μg
E) Human granulocyte gangliosides (HGG): 10, 5, 2.5, 1.25 and 0 μl FIGS. 10A and 10B: Identification of specific antibodies agains the ganglioside antigen used for immunisation Test of different hybridoma clones for the production of IgM (A) and IgG (B) in ELISA after thinning out. ELISA was carried out as described in example 8. The incubation time of the substrate solution was varied (15 min, 30 min, 45 min, 60 min, 120 min and 180 min). Clones 33.3, 33.5 and 33.6 showed a clear titer on IgM (A). A titer on IgG could not be detected in any of the tested clones (B).

Figure 10A:
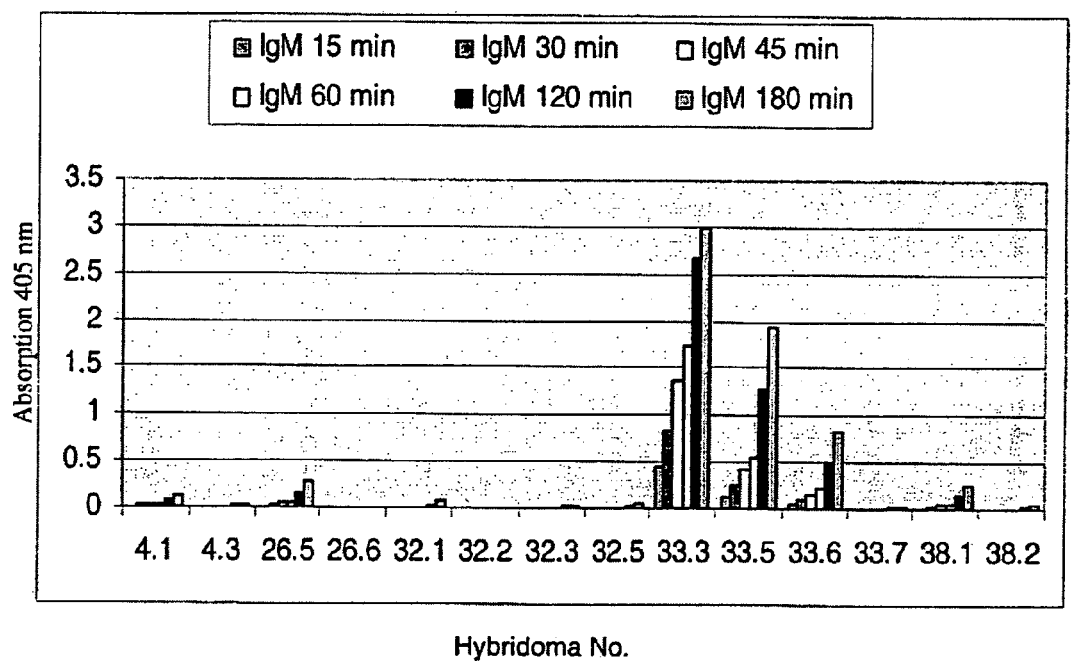
Figure 10B:
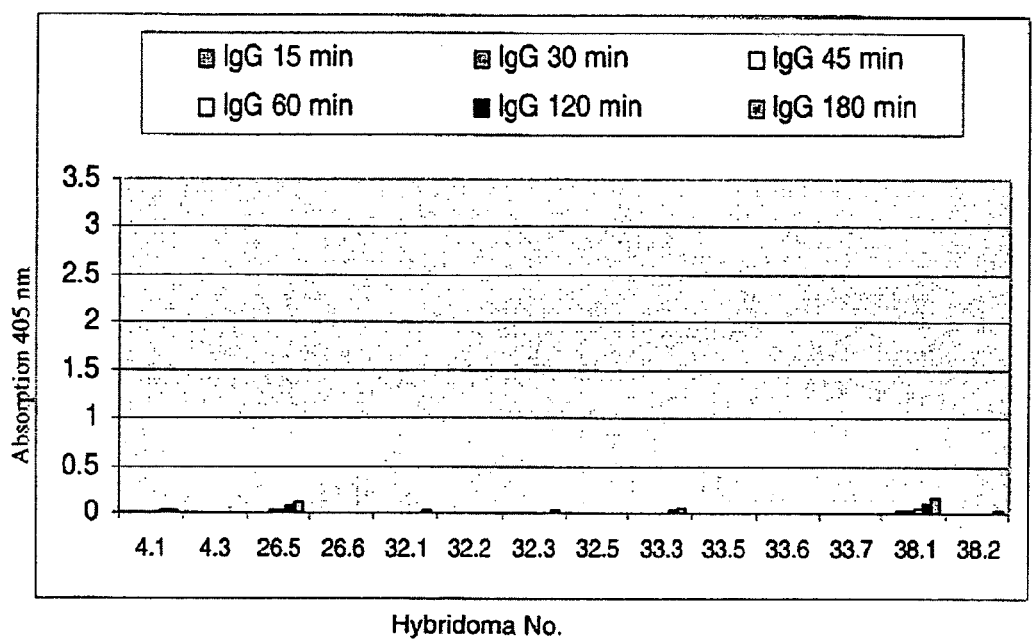
Figure 11:
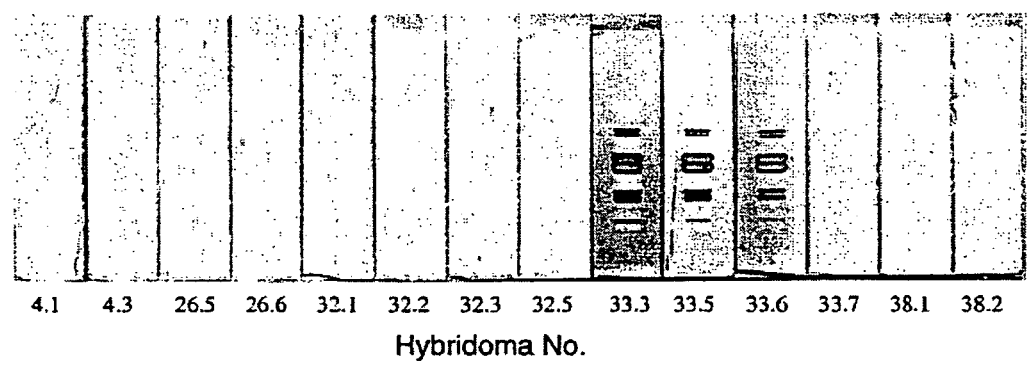

FIG. 11: Characterisation of anti-α2-6 sialylated monoclonal ganglioside antibodies of the neolacto type TLC overlay assay for the characterisation of the recognition motif of the mAb clones. The clones which have already been depicted in FIG. 10 were, as described in example 2, examined for their recognition motif in order to detect human granulocyte gangliosides (4 μg/lane) which were separated on the DC plates. Clones 59.33.3, 59.33.5 and 59.33.6 show the binding or recognition motif identical to rViscumin.

Figure 12:
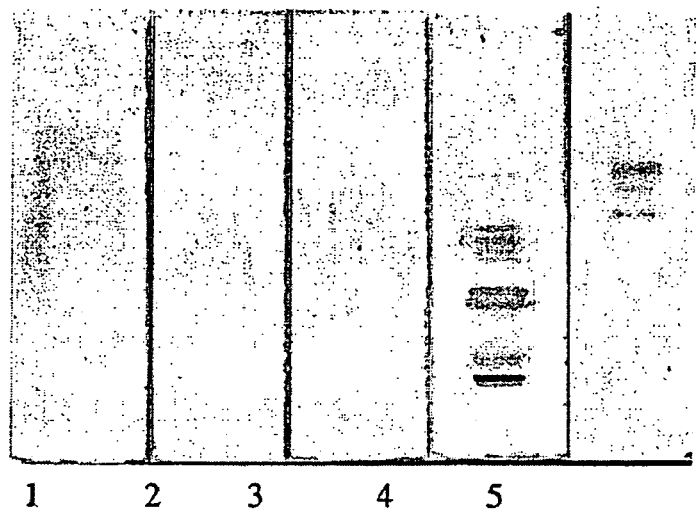
Figure 12:
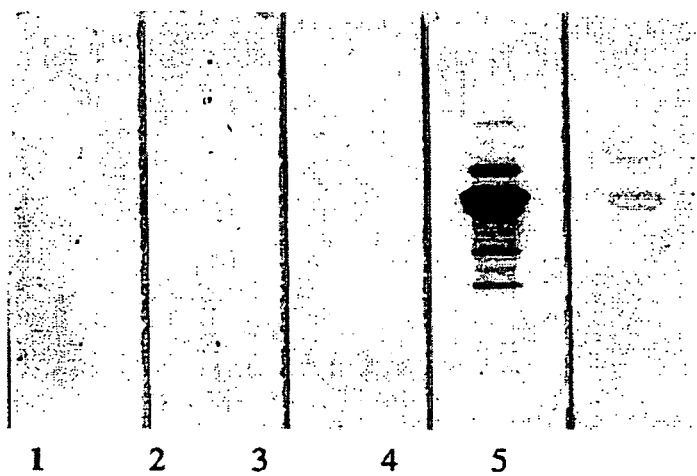
Figure 12:
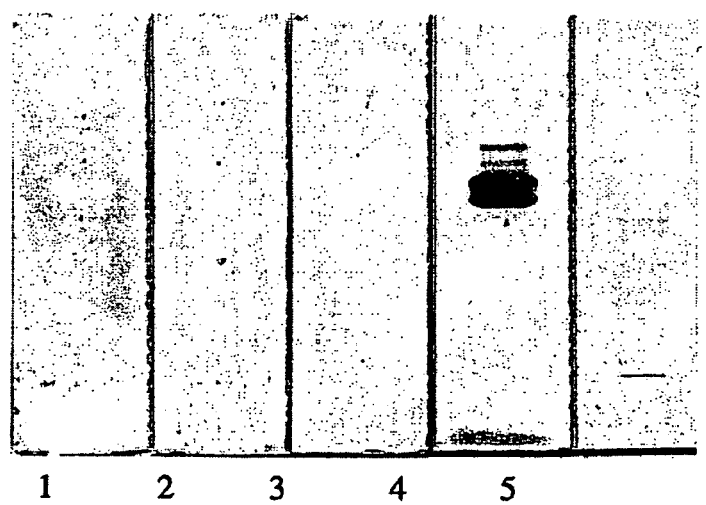

FIGS. 12A, 12B and 12C: Further characterisation of anti-α2-6 sialylated monoclonal ganglioside antibodies of the neolacto type TLC overlay assays with (A) isolated neutral GSL of the neolacto series from human granulocytes (15 μg per lane), (B) of the globo series (from human erythrocytes; 10 μg per lane) and (C) of the ganglio series (from MDAY-D2 cells; 10 μg per lane). The experimental proceeding is described in example 9. In the first three lanes each of FIGS. 12A to C mAb clones 50.33.3, 59.33.5 and 59.33.6 were used. The positive controls in lanes 4 of FIGS. 12A-C reflect the reactions with specific antibodies against each of the terminal sugar structures of the applied neutral GSL. In lanes 5 a polyclonal antiserum from goat (cf. Müthing et al., Glycobiology 12, 485-497) is tested. A cross-reactivity of the mAb clones tested in lanes 1 to 3 can be ruled out.

Figure 13:
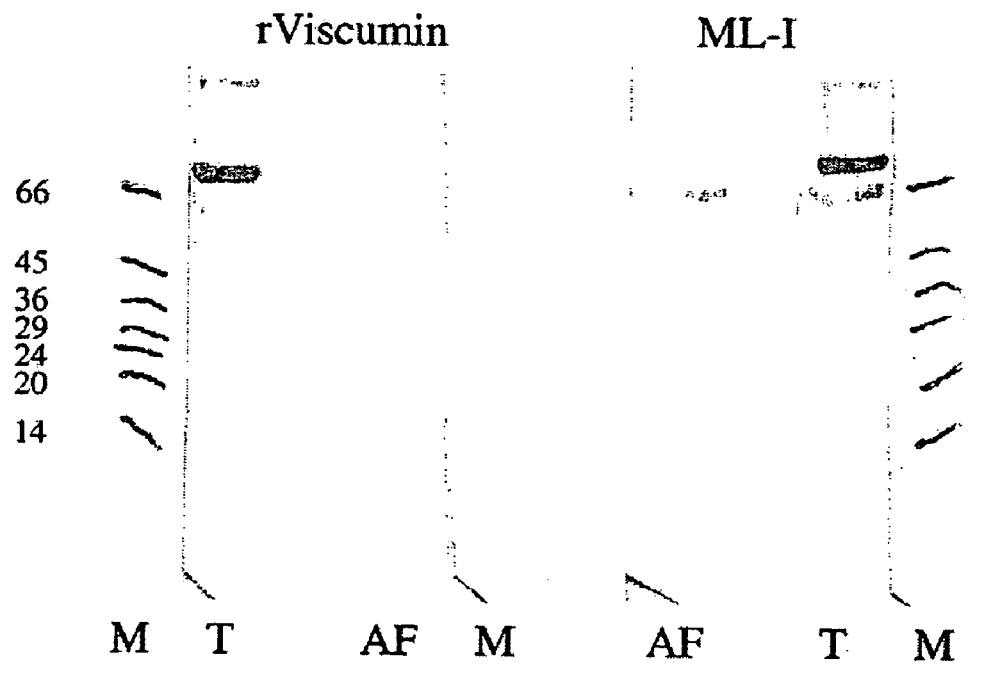

FIG. 13: Detection of CD75s recognition of rViscumin on glycoproteins.

1 μg each of the corresponding proteins, in lane T: transferring, soluble protein with Neu5Acα2-6Galβ1-4GlcNAc residues, and in lane AF: asialofetuin, (Galβ1-4GlcNAc-residues and Galβ1-3GalNAc-Ser/Thr) were applied on SDS gel and subsequently transferred onto a nitrocellulose membrane. In a Western blot technique it was then tried to detect the CD75s structure with rViscumin (1 μg/ml) and subsequently with the anti-A-chains mAb TA5 and anti-mouse IgG labelled with alkaline phosphatase (cf. example 2). M reflects traces of the label. The molecular weights are indicated in kDa.

Figure 14:
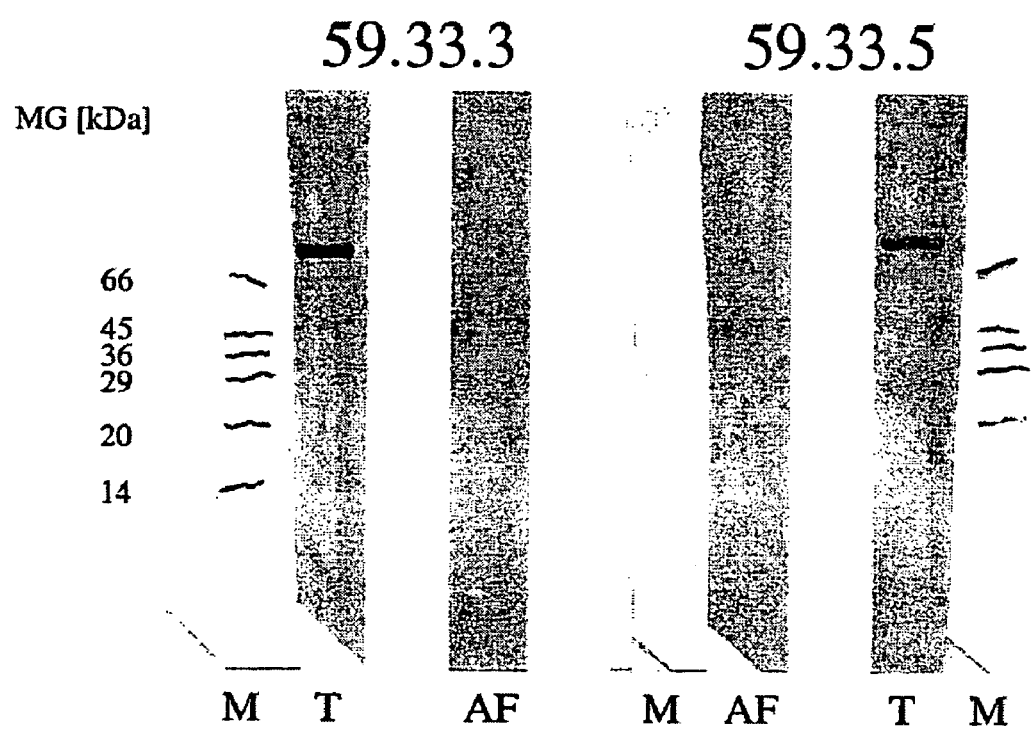

FIG. 14: Detection of CD75s recognition of rViscumin on glycoproteins.

1 μg each of the corresponding proteins, in lane T: transferring, soluble protein with Neu5Acα2-6Galβ1-4GlcNAc residues, and in lane AF: asialofetuin, (Galβ1-4GlcNAc-residues and Galβ1-3GalNAc-Ser/Thr) were applied on SDS gel and subsequently transferred onto a nitrocellulose membrane. In a Western blot it was then tried to detect the CD75s structure with with mAb 59.33.3 and 59.33.5 as described in example 9.

TABLE 1

| Structure | Abbr. | rViscumin | Ricin |
|---|---|---|---|
| Gangliosides | | | |
| Neu5Acα2-3Galβ1-4Glcβ1-1Cer | GM3 | – | – |
| Galβ1-3GalNAcβ1-4(Neu5Acα2-3)Galβ1-4Glcβ1-1Cer | GM1 | – | (+) |
| Neu5Acα2-3Galβ1-3GalNAcβ1-4(Neu5Acα2-3)Galβ1-4Glcβ1-1Cer | GD1a | – | – |
| Galβ1-3GalNAcβ1-4(Neu5Acα2-8Neu5Acα2-3)Galβ1-4Glcβ1-1Cer | GD1b | – | – |
| Neu5Acα2-3Galβ1-3GalNAcβ1-4(Neu5Acα2-8Neu5Acα2-3)Galβ1-4Glcβ1-1Cer | GT1b | – | – |
| Neu5Acα2-3Galβ1-4GlcNAcβ1-3Galβ1-4Glcβ1-1Cer | IV³nLc4 | – | – |
| Neu5Acα2-6Galβ1-4GlcNAcβ1-3Galβ1-4Glcβ1-1Cer | IV⁶nLc4 | +++++ | – |
| Neu5Acα2-3Galβ1-4GlcNAcβ1-3Galβ1-4GlcNAcβ1-3Galβ1-4Glcβ1-1Cer | VI³nLc6 | – | – |
| Neu5Acα2-6Galβ1-4GlcNAcβ1-3Galβ1-4GlcNAcβ1-3Galβ1-4Glcβ1-1Cer | VI⁶nLc6 | +++++ | – |

TABLE 1-continued

| Structure | Abbr. | rViscumin | Ricin |
|---|---|---|---|
| Neutral Glycosphingolipids | | | |
| Galβ1-4Glcβ1-1Cer | Lc2 | (+) | + |
| Galα1-4Galβ1-4Glcβ1-1Cer | Gb3 | – | (+) |
| GalNAcβ1-3Galα1-4Galβ1-4Glcβ1-1Cer | Gb4 | – | – |
| GalNAcβ1-4Galβ1-4Glcβ1-1Cer | Gg3 | – | – |
| Galβ1-3GalNAcβ1-4Galβ1-4Glcβ1-1Cer | Gg4 | – | +++ |
| Galβ1-4GlcNAcβ1-3Galβ1-4Glcβ1-1Cer | nLc4 | – | +++++ |
| Galβ1-4GlcNAcβ1-3Galβ1-4GlcNAcβ1-3Galβ1-4Glcβ1-1Cer | nLc6 | – | +++++ |
| Galβ1-4(Fucα1-3)GlcNAcβ1-3Galβ1-4GlcNAcβ1-3Galβ1-4Glcβ1-1Cer | Lewis$^x$ | – | – |

The following examples illustrate the invention described.

EXAMPLE 1

Figure 3:
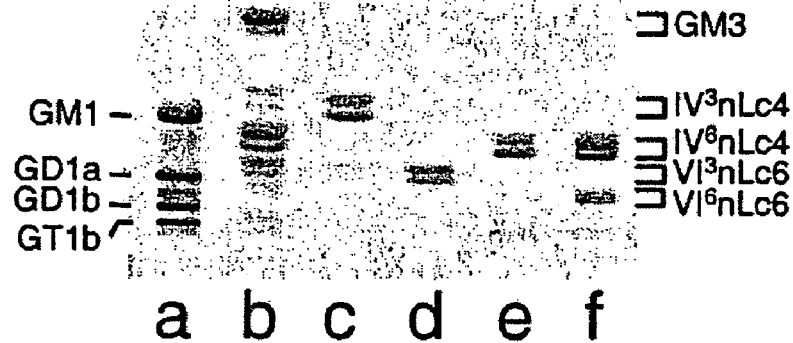
Figure 3:
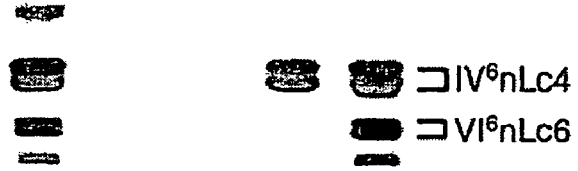
Figure 3:
Figure 4:
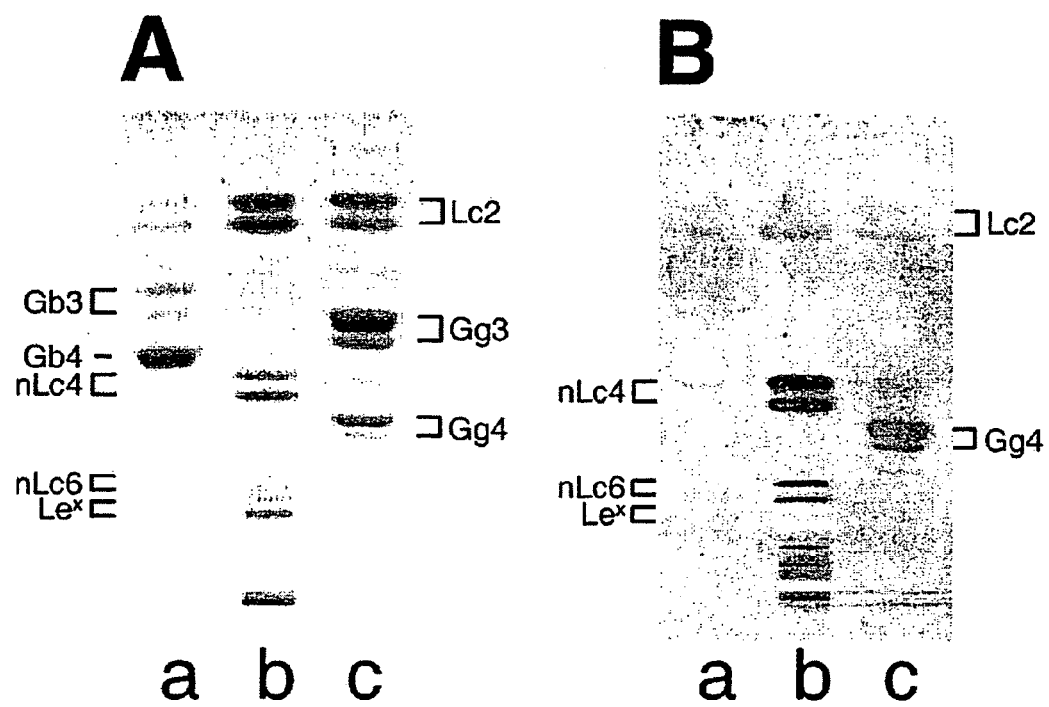
Figure 5:
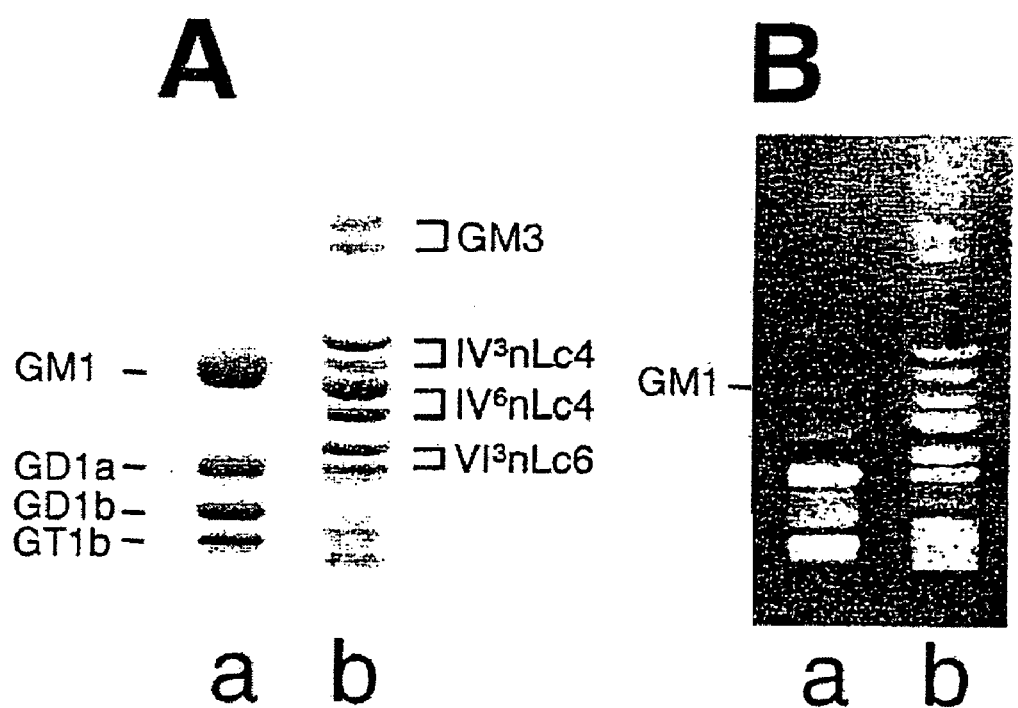

Thin-Layer Chromatography for the Separation and Detection of Glycosphingolipids and for Specifically Detecting Them Neutral GSL were recovered from human granulocytes, human erythrocytes and MDAY-D2 cells and gangliosides from human granulocytes and human brain (FIGS. 2, 4, 5 and 7) or HPLC-purified samples were used for the analysis (FIG. 3). The corresponding samples were separated on a thin-layer chromatography plate (HPTLC plates, 10×10 cm, 0.2 mm thickness by Merck, Darmstadt # 5633) coated with silica gel. Neutral GSL were separated in solvent 1 (chloroform/methanol/water, 120/70/17 v/v/v) and glangliosides in solvent 2 (chloroform/methanol/water 120/85/20 v/v/v+2 mM $CaCl_2$). Neutral GSL were stained with orcinol, gangliosides were either stained with orcinol or with resorcinol (Svennerholm, 1956, 1957). Neutral GSL of human granulocytes and MDAY-D2 cells and also of gangliosides of human granulocytes appear as double bands on the DC plate.

In order to identify the individual gangliosides, an immune-staining procedure according to Müthing and Mühlradt (1988) and Müthing (1998) was carried out with specific antisera. Terminal α2-6-sialylated gangliosides of the neolacto series were identified with a polyclonal anti-IV$^6$nLc4Cer antiserum. To this avail, the plate was first fixed with polyisobutylmethacrylate (Röhm, Darmstadt). Subsequently, the plate was blocked in PBS (20 mM phosphate, 150 mM NaCl, pH 7.2)+1% BSA (solution A). In the following, the above-identified polyclonal antiserum was used in a dilution of 1:1,000 in solution A and subsequently washed 3× with solution B (PBS+0.05% Tween 20). Bound antiserum is detected with secondary antiserum rabbit-anti-chicken-IgY in a dilution of 1:2,000 in solution A. Afterwards, it is washed 3× with solution B and 1× with glycine buffer (0.1 M glycine, 1 mM ZnCl2, 1 mM MgCl2, pH 10.4). The detection is carried out with 0.05% (w/v) 5-brome-4-chloro-3-indolylphosphate in glycine buffer. The control gangliosides which were used in the different TLC tests and which are characterised in detail and which were used as reference material for the identification of the gangliosides which are specific of rViscumin originated from different isolations from human blood cells or cell cultures (Müthing et al., 1994; Müthing and Kemminer, 1996; Schwartz et al., 1985; Müthing and Cacic, 1997).

EXAMPLE 2

TLC Test for the Specific Detection of Carbohydrate-Binding Proteins, such as Ricin and rViscumin, Bound to Neutral GSL or Gangliosides Neutral GSL or gangliosides which were separated on a thin-layer chromatography plate were washed with PBS-Tween 80 (0.1 g/L Tween 80 in PBS). Subsequently, a coating with rViscumin or ricin protein solution (1 μg/ml in PBS-T80) was carried out and an incubation was carried out for 1 hour. Subsequently, washing was carried out with solution B (cf. example 1) and then the plate was incubated for 15 min in solution A (cf. example 1). Subsequently, the bound rViscumin was recognised with the monoclonal Ab TA5 (1 μg/ml in solution A) described by Tonevitzky et al. 1995, or the bound ricin was recognised by a rabbit-anti-ricin antiserum by Sigma #R-1254 (1:20.0 dilution in solution A). The detection of the bound antibodies was carried out as described in example 1 with the secondary antibodies against mouse or rabbit immunoglobulin which were needed in each case.

EXAMPLE 3

Comparison of the Sensitivity of Different Cell Lines to rViscumin

Cultivation: CHO-K1 cells (ATCC CCL-81) and HL-60 cells (ATCC CCL-240) were grown in a 1:1 mix of DMEM and Ham's F12 medium. The human bladder carcinoma cell line 5637 (ATCC HTB-9) was cultured in RPMI 1640. A cultivation of the cells was carried out under standard conditions as described in Möckel et al., 1997. The sensitivity of the cell lines to rViscumin was established in an in-vitro-cytotoxicity test. $8\times10^3$ 5637, $1\times10^4$ CHO-K1 and $1.8\times10^4$ HL-60 each per well were plated in 96-well plates (Nunc) and incubated with increasing concentration of rViscumin in a final volume of 100 μl for 72 h at 37° C. under a 10% $CO_2$ atmosphere. All measurements were carried out with sixfold determination. After 72 hours, 10 μl WST-1 was added by a pipette in order to detect living cells (Ishiyama et al., 1993; Möckel et al., 1997). The cells were incubated with the colouring salt for 4 hours at 37° C. and subsequently measured at 450 nm in Thermomax by Molecular Devices. In this connection, the amount of dye is directly proportional to the number of living cells. In FIG. 6 the viability curves of the different cell populations are applied against increasing rViscumin concentrations.

Figure 7:
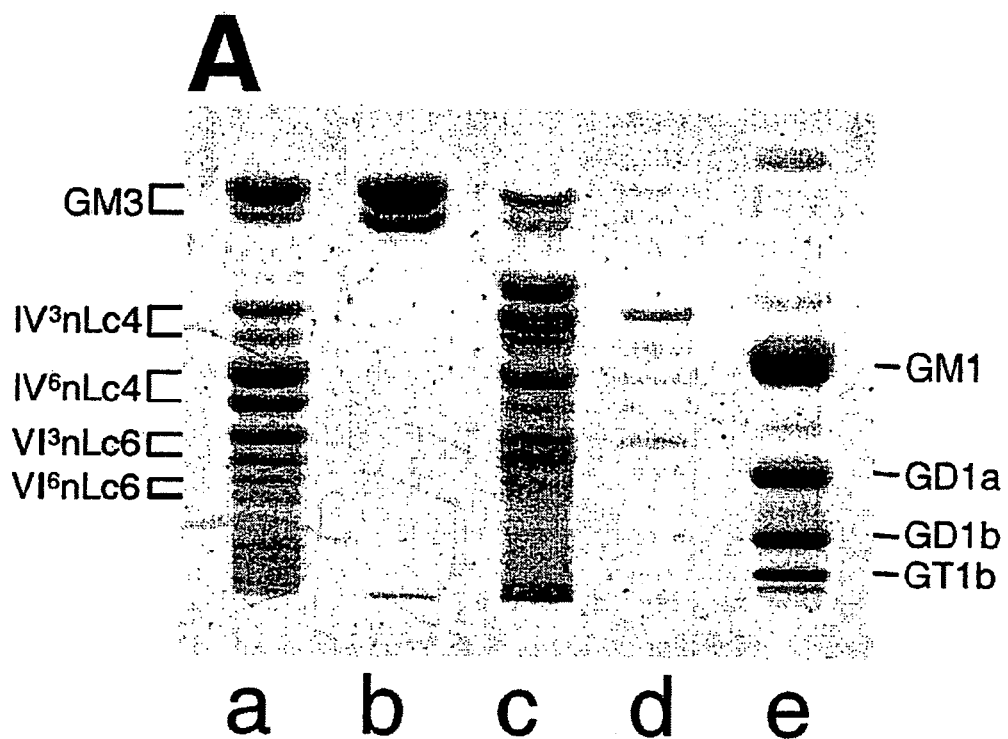
Figure 7:
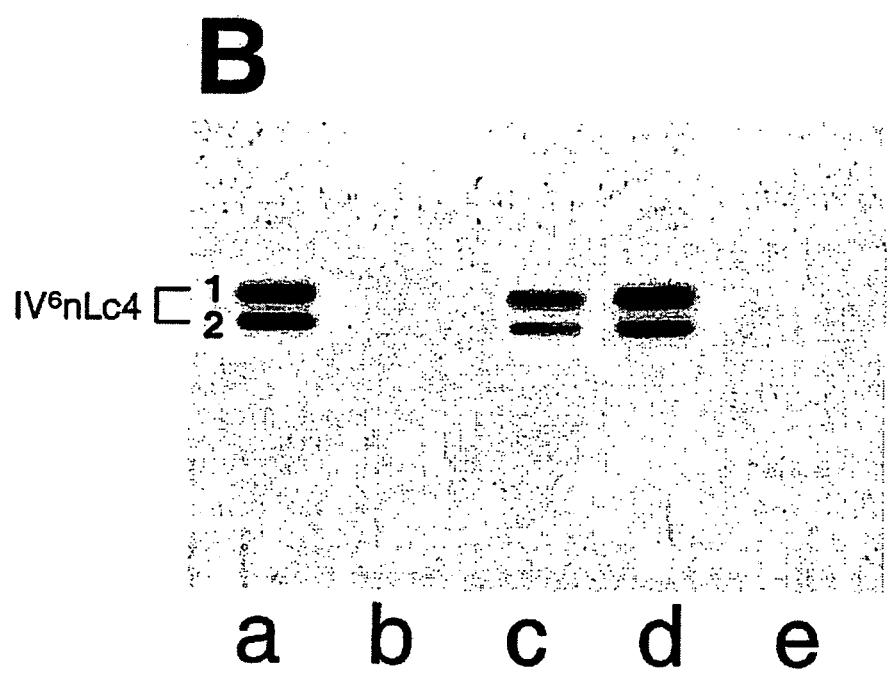

The cell line HL-60 (points) is a human promyeloic cell line which reacts very sensitively with an $IC_{50}$ value of 66 pg/ml to rViscumin. In the bladder carcinoma cell line 5637 (triangles), an $IC_{50}$ of 690 pg/ml was measured, the hamster cell line CHO K1. (open circles) showed no sensitivity to rViscumin up to a tested concentration of 300 ng/ml. The sensitivity of the different cell lines to rViscumin could be correlated with the occurrence of the potential receptor in FIG. 7. FIG. 7A shows an orcinol-stained thin-layer chromatogram of the complete ganglioside fractions of the cell lines used in each case. FIG. 7B shows the specific immunologic detection of the potential rViscumin receptors with an anti-Neu5Acα2-6Galβ1-4GlcNAc-R antiserum (overlay assay). In lanes b, c and d of FIG. 7B, ganglioside amounts of identical cell numbers of CHO-K1, 5637 and HL-60 cells, respectively, are applied. The CHO-K1 cells, which are insensitive to rViscumin show no specific band on the level of the potential receptor in lane b of FIG. 7B, while, with the same number of cells applied, the most sensitive cell line (HL-60) shows the strongest double band. From the different specificities of the lectins examined which were observed in the TLC overlay assays conclusions can be drawn on the binding behaviour of ricin and mistletoe lectin (particularly rVisumin) to their receptors in vivo or in cell cultures. The examples describe that the CHO-K1 cell line is insensitive to a tested rViscumin concentration of up to 300 ng/ml (cf. FIG. 6). By introducing the gangliosides which are specific for rViscumin into the membranes of the CHO-K1 cells (Neu5Ac α2-6 Gal structures), these cells which are very insensitive to rViscumin were, however, sensibilised (cf. FIG. 8).

EXAMPLE 4

Sensibilisation of Cell Lines by Preincubation with Specific Gangliosides (cf. FIG. 8)

CHO-K1 cells were sown with a cell density of $5\times10^3$ cells per well in 96-well plates. The cells were cultivated for 24 hours in a serum-free X-Vivo culture medium (Biowhittaker) at 37° C. Subsequently, the medium was discarded and was replaced by X-Vivo culture medium containing 0 (control), 25, 50, 100 and 200 μM of a human granulocyte ganglioside fraction. In order to incorporate the gangliosides into the membrane of the CHO-K1 cells, the cells were kept for 48 hours at 37° C. under cell culture conditions. Subsequently, the cells were either extensively washed with serum-free X-Vivo or with 5% FCS-containing X-Vivo. Then, the cells were treated with rViscumin (300 ng/ml) for 48 hours. The viability of the cells was quantified with WST-1 staining and were correlated with the untreated control (without addition of rViscumin and gangliosides). The samples were grown on in triplicates with an end volume of 100 μl per well.

EXAMPLE 5

Purification of Gangliosides of In-Vitro Propagated Cells and Correlation of the Occurrence of Specific Gangliosides in Cell Lines and Sensitivity to rViscumin Showing the cell mass for the subsequent isolation of GSL or gangliosides: CHO-K1 cells (ATCC CCL-81) and HL-60 cells (ATCC CCL-240) were grown in a 1:1 mix of DMEM and Ham's F12 medium. The cells were cultivated in the presence of 50 mg/L gentamycin and 2.5 mg/L amphotericin B. A cultivation of 5637-cells was carried out in 175 $cm^2$-flasks. HL-60 and CHO-K1 cells were cultivated in a 1 L-Spinner flask as described in Duvar et al. (1996) and Müthing et al (1996b). The physiological parameters were: 37° C., pH 7.2, fumigation with oxygen, stirring velocity: 40 rpm. The cells were harvested after reaching the final cell densities, washed twice with PBS and subsequently subjected to a chloroform/methanol extraction (cf. example 1). The human bladder carcinoma cell line 5637 (ATCC HTB-9) was cultivated in RPMI 1640. The gangliosides were isolated on DEAE sepharose CL-6B with standard procedures using anion exchanger chromatography, as described by Ledeen and Yu (1982), Müthing et al. (1987) or Duvar et al (1997). For saponification of the phospholipids, the gangliosides were incubated for 1 hour at 37° C. in 1 N NaOH. Subsequently, the ganglioside fraction was neutralised with acetic acid and dialysed. A further purification step followed by adsorption chromatography to latrobeads 6RS-8060 (Macherey & Nagel, Düren, Germany) (Ueno et al., 1987). When the ganglioside fraction was subsequently separated from the cell lysates, it was always assumed that the number of cells was always approximately the same. Thus, it was possible to make a semiquantitative statement with respect to the presence of the specific ganglioside. The detection was carried out immunologically as described in example 1 with a polyclonal anti-$IV^6$nLc4Cer antiserum.

EXAMPLE 6

Purification of Terminal α2-3- and α2-6-Sialated Gangliosides of the Neolacto Series A column filled with Fractogel EMD TMAE-650-S (MERCK, Darmstadt) is filled with the gangliosides from human granulocytes (HGG). TMAE-bound gangliosides are eluated with a linear gradient to ammoniumacetate, pooled and deionized. Four fractions with terminal α2-3-sialated (HGG1 and HGG2) and terminal α2-3-sialated neolacto type monosialogangliosides (HGG3 and HGG4) were obtained. All gangliosides were separated on thin-layer chromatograms as double band. The differences are due to the ceramide unit, which, in the case of the upper band, esterified a C24 fatty acid and, in the case of the lower band, a C16 fatty acid. The structures of all gangliosides which can be depicted with the methods have already been characterised (Müthing et al., 1993; Müthing et al., 1996, Metelmann et al., 2000). The purified gangliosides have been separated in FIG. 3 and were referred to for the closer specification of the carbohydrate-binding specificity of rViscumin.

EXAMPLE 7

Enzyme-Linked Lectin Assay (ELLA)

The ELLA was coated in plates which are coated with the corresponding neutral GSL or gangliosides (NUNC MaxiSorp F96, Wiesbaden) at room temperature. The wells were filled with the corresponding GSL in 100 μl methanol. Starting from a GSL stock solution, 1:2 dilutions were prepared. This contains the following GSL: neutral GSL of human erythrocytes: 10, 5, 2.5 and 1.25 μg; neutral GSL of human granulocytes: 15, 7.5, 3.75 and 1.9 μg; neutral GSL from MDAY-D2 cells: 20, 10, 5 and 2.5 μg; human brain gangliosides (HBG): 10, 5, 2.5 and 1.25 μg; human granulocyte gangliosides (HGG): 10, 5, 2.5 and 1.25 μg. Subsequently, the methanol was evaporated in a dry atmosphere (45 min at 37°

C.). All further steps were carried out as in the TLC overlay assay described in example 2. All incubations were carried out in a volume of 100 µl. The GSL-coated plates were incubated for 15 min with PBS-Tween 80® (0.01 mg/ml) and subsequently incubated with 1 µg rViscumin (dissolved in PBS-Tween 80) for 1 hour. Afterwards, the plates were washed with PBS-Tween 20® (0.01 mg/ml) and then incubated with PBS for 15 minutes. Subsequently, the samples were incubated with murine anti-ML-1 A monoclonal antibody TA5 (1 µg/ml in PBS) for 1 hour. After again washing for three times with PBS-Tween 20®, an incubation in PBS with an anti-mouse IgG (alkaline phosphatases coupled) in a 1:2000 dilution was carried out for 1 hour. After again washing for three times with PBS-Tween 20®, a colorimetric detection is carried out with a reaction of the substrate disodium-4-nitrophenylphosphate×6H$_2$O (16 mM in 0.1 M glycine buffer, pH 10.4). The plate was measured after an incubation for 20 minutes at 25° C. at 405 nm in a microtiter plate reader.

Unexpectedly, a binding of rViscumin could only be found to such glycosphingolipids (GSL) which terminally exposed an α2-6-bound galactose to GSL of the neolacto series at the Neu5Ac (HGG fraction from human granulocytes). All other neutral GSL from different sources (human granulocytes and erythrocytes, MDAY-D2 cells), each with terminal galactose residues and human brain gangliosides of the ganglio series showed no binding even in the highest concentration used.

EXAMPLE 8

Production of Monoclonal Antibodies Against α2-6-Sialylated Gangliosides of the Neolacto Type The α2-6-sialylated gangliosides of the neolacto type were isolated from leucocytes (buffy coat from whole blood). The purification of the gangliosides was carried out as described in example 5. In the further process, these α2-6-sialylated gangliosides of the neolacto type served as antigens for the immunisation of 2×3 mice. As the antigens have no immunogenic effect alone due to their lack in size, they are administered to the mice with so-called haptenes. In this connection, two methods were carried out in parallel. In method 1 methyl-BSA was used as hapten in a concentration of 1 mg/ml. The three mice received different amounts of the antigen (5, 10 and 20 micrograms) The mice were immunised in known intervals and received a booster altogether two'further times with an interval of 10 days. In method 2 a mixture of liposomes and lipopolysaccharide (LPS) was used as hapten. Here, too, different amounts of the antigen (5, 10 and 20 microgams) were administered to the mice on three application days, each, with an interval of 10 days.

From the altogether six mice which were immunised with the help of two methods, a positive titer against the antigen could be detected in the blood of three of the mice. The preparations with the hapten methyl-BSA were negative. The preparations with the hapten lipopolysaccharide in liposomes were all positive, independent of the dose of the antigen administered. A mouse was sacrificed and the spleen cells were used for fusion. The supernatants of the fusion assays were examined in the DC-overlay assay (as described in examples 1 and 2) and in ELISA. In this process the microtiter plate was coated with 1 µg HGG gangliosides (human granulocyte gangliosides) in 50 µl methanol as described in example 7. 50 µl of the corresponding plasma samples or supernatants of the fusion assays were applied undiluted to the coated plates and were incubated for 60 minutes at 25° C. Subsequently, washing was carried out 3 times with PBS-T. A detection of IgM or IgG was carried out with an anti-mouse-IgG or an anti-mouse-IgM antibody which was labelled with alkaline phosphatase. A reaction of the substrate p-NPP was carried out as described in example 7. Fusion assays with a positive titer were subsequently thinned out on the clone level. FIG. 10A shows a detection for three positive IgM clones (59.33.3, 59.33.5 and 59.33.6). All cones were also examined for the production of IgG, however, they showed no positive reaction to IgG (FIG. 10B).

EXAMPLE 9

Characterisation of anti-α2-6-Sialylated Monoclonal Ganglioside Antibodies of the Neolacto Type α2-6-sialylated gangliosides of the neolacto type always carry a Neu5Acα2-6-Gal at their end. Another motif, which was also described in the course of this invention, comprises the ganglioside structure Neu5Acα2-6-Galβ1-4GlcNAc-R; wherein "R" represents a residue. This motif has been described in the literature as CD75s (Schwartz-Albiez (2000), J. Biol. Regul. Homeost. Agents 14, 284-285). FIG. 11 shows DC-overlay assays with various IgM clones which were tested in ELISA as described in example 8. Here, the gangliosides from human granulocytes (HGG) were separated with the help of thin-layer chromoatography. The assay was carried out as described in example 2. Here, 4 µg HGG were separated. The detection of anti-CD75s mAk bound to the plate was carried out as described in example 8. Clones 59.33.3, 59.33.5 and 59.33.6 showed a positive signal in this test, too. All three clones recognised the same gangliosides (IV6nLC4 and IV6nLC6) and, thus, had a binding behaviour identical to rViscumin (FIG 2Bb). A cross-reactivity of the three antibodies against the core part of the sugar structures, which could possibly be expected, could be ruled out experimentally by using isolated neutral GSL from either the neolacto series from human granulocytes (15 µg per lane; FIG 12A) or the globo series (from human erythrocytes, 10 µg per lane in FIG 12B) and the ganglio series (from MDAY-D2 cells; 10 µg per lane; in FIG 12C). The experimental approach was identical to the one described above. In the first three lanes, each, of FIG. 12A to C, no signals could be detected by using the mAb clones 59.33.3, 59.33.5 and 59.33.6. In all three cases did the absence of the terminal α2-6-linked sialic acid lead to the absence of a specific signal. The positive controls in lanes 4 of FIG. 12A to C reflect the reactions with specific antibodies against the respective terminal sugar structures of the neutral GSL applied. In lanes 5 a polyclonal antiserum from goat (cf. Müthing (2002) Glycobiology 12, 485-497) was carried along. This antiserum which was originally prepared against α2-6-sialylated gangliosides of the neolacto type shows a cross-reactivity against many of the antigens which were applied here, which could lead to false positive signals, particularly when using this antiserum in the examination of material from patients. The results with the monoclonal antibodies 59.33.3, 59.33.5 and 59.33.6, shown in lanes 1 to 3, where such undesired cross-reactivites did not occur, have to be considered more important. The mAb-clone 59.33.3 was deposited with the DSMZ in Brunswick on 20 Dec. 2002 under the accession number ACC2580 according to the Budapest Treaty.

EXAMPLE 10

Detection of CD75s on Glycoproteins

The monoclonal antibodies 59.33.3 and 59.33.5 (FIG. 14) and rViscumin (FIG. 13) themselves were examined for their usability for the detection of CD75s motifs on glycoproteins. Here, 1 μg, each, of the corresponding proteins, in lane T: transferring, soluable protein with Neu5Acα2-6Galβ1-4G1cNAc-residues and in lane AF: asialofetuin, (Galβ1-4GlcNAc residues and Galβ1-3GalNAc-Ser/Thr) were applied to the SDS gel and subsequently transferred to a nitrocellulose. In a Western blot it was then tried to detect the CD75s structure either with rViscumin (1 μg/ml) and subsequently with the anti-A-chain mAb TA5 and with the anti-mouse-IgG labeled with alkaline phosphatese (cf. example 2). In the case of the examination of the bond/recognition of the CD75s epitope by the mAb 59.33.3 and 59.33.5, after the transfer of the proteins to the nitrocellulose, the same was done as described in example 9. The transferring is unambiguously recognized by the mAbs 59.33.3 and 59.33.5 and by rViscumin.

Both antibody clones 59.33.3 and 59.33.5 tested recognise CD75s motifs on the glycoprotein transferrin as epitopes.

Literature:

Agapov, I. I., Tonevitsky, A. G., Shamshiev, A. T., Phol, E., Pohl, P., Palmer, R. A., Kirpichnikov, M. P., (1997): The role of structural domains in RIP II Toxin model membrane binding. FEBS Lett., 402, 91-93

Andre S., Unverzagt, C., Kojima, S., Dong, X., Fink, C., Kayser, K., Gabius, H. J. (1997) Neoglycoproteins with the synthetic complex biantennary nonasaccharide or its alpha 2,3/ alpha 2/6-sialylated derivatives: their preparation, assessment of their ligand properties for purified lectins, for tumor cells in vitro, and in tissue sections, and their biodistribution in tumor-bearing mice. Bioconjug Chem 8, 845-855

Barbieri, L., Battelli, M. G. and Stirpe, F. (1993) Ribosome-inactivating proteins from plants. Biochim. Biophys. Acta, 1154, 237-282.

Beuth J, Ko H L, Gabius H J, Pulverer G. (1991) Influence of treatment with the immunomodulatory effective dose of the beta-galactoside-specific lectin from mistletoe on tumor colonization in BALB/c-mice for two experimental model systems. In Vivo; 5(1); 29-32

Beuth J, Ko H L, Gabius H J, Burrichter H, Pulverer G. (1992) Behavior of lymphocyte subsets and expression of activation markers in response to immunotherapy with galactoside-specific lectin from mistletoe in breast cancer patients. Clin. Investig.; 70(8): 658-61.

Beuth J, Ko H L, Tunggal L, Geisel J, Pulverer G. (1993) [Comparative studies on the immunoactive action of galactoside-specific mistletoe lectin. Pure substance compared to the standardized extract]. Arzneimittelforschung.; 43(2);166-9. German language.

Bocci V. (1993) Mistletoe (viscum album) lectins as cytokine inducers and immunoadjuvant in tumor therapy. J Biol Regul Homeost Agents; 7(1; 1-6.

Bonk, Biopsie und Operationspräparat; Manual for doctors and students

Critchley, D. R. Dtreuli, C. H., Kellie, S., Ansell, S., and Patel., B. (1982): Characterisation of the cholera toxin receptor on Balb/c 3T3 cells as a ganglioside similar to, or identical with, ganglioside GM1. No evidence for galactoproteins with receptor activity. Biochem J., 204, 209-219

Debray, H., Montreuil, J. and Franz, H. (1994) Fine sugar specificity of the mistletoe (Viscum album) lectin I. Glycoconjugate J., 11, 550-557.

Dulat, H J., von Grumbkow, C, Baars, W., Schroder, N., Wonigeit, K., Schwinzer, R. (2001) Down-regulation of human alloimmune responses by genetically engineered expression of CD95 ligand on stimulatory and target cells. Eur J Immunol., 7, 2217-26

Duvar, S., Müthing, J., Mohr, H. and Lehmann, J. (1996) Scale up cultivation of primary human umbilical vein endothelial cells on microcarriers from spinner vessels to bioreactor fermentation. Cytotechnology, 21, 61-72.

Duvar, S., Peter-Katalini, J., Hanisch, F.-G. and Müthing, J. (1997) Isolation and structural characterization of glycosphingolipids of in vitro propagated bovine aortic endthelial cells. Glycobiology, 7, 1099-1109.

Eck, J., Langer, M., Möckel, B., Baur, A., Rothe, M., Zinke, H. and lentzen, H. (1999a) Cloning of the mistletoe lectin gene and characterization of the recombinant A-chain. Eur. J. Biochem., 264, 775-784.

Eck, J., Langer, M., Möckel, B., Witthohn, K., Zinke, H, and Lentzen, H. (1999b) Characterization of recombinant and plant-derived mistletoe lectin and their B-chain. Eur. J. Biochem., 265, 788-797.

Endo Y, Oka T, Tsurugi K, Franz H. (1989) The mechanism of action of the cytotoxic lectin from Phoradendron californicum: the RNA N-glycosidase activity of the protein. FEBS Lett.; 248(1-2): 115-8.

Franz, H. (1986) Mistletoe lectin and their A and B chains. Oncology, 43, 23-24.

Frantz, M., Jung, M. L., Riberau-Gayon, G., and Anton, R. (2000) Modulation of mistletoe lectin (Viscum album L.) Ictins cytotoxicity by carbohydrates and serum glycoproteins. Arzneimittelf./Drug Res. 50, 471-478

Gabius H J, Gabius S, Joshi S S, Kruip J, Kojima S, Gerke V, Kratzin H, Gabius S. (1992) The immunomodulatory beta-galactoside-specific lectin from mistletoe: partial sequence analysis, cell and tissue binding, and impact on intracellular biosignalling of monocytic leukemia cells. Anticancer Res.; 12(3) 669-75.

Gabius H J, Gabius S, Joshi S S, Koch B, Schroeder M, Manzke W M, Westerhausen M. (1994) From ill-defined extracts to the immunomodulatory lectin: will there be a reason for oncological application of mistletoe?Planta Med., 60(1): 2-7.

Gabius H J und Gabius S; Die Misteltherapie auf dem naturwissenschaftlichen Prüfstand. P Z., 1994; 139. 9-16.

Galanina, O. E., Kaltner, H., Khraltsova, L. S., Bovin, N. V. and Gabius, H.-J. (1997) Further refinement of the description of the ligand-binding mistletoe lectin, a plant agglutinin with immunomodulatory potency. J. Mol. Recogn., 10, 139-147.

Ganguly C and Das S. (1994) Plant lectins as inhibitors of tumour growth and modulators of host immune response. Chemotherapy; 40(4): 272-8.

Gilleron, M., Siebert, H.-C., Kaltner, H., von der Lieth, C.-W., Kozar, T., Halkes, K. M., Korchagina, E. Y., Bovin, N. V., Gabius, H.-J. and Vliegenthart, J. (1998) Conformer selection and differential restriction of ligand mobility. Eur. J. Biochem., 252, 416-427.

Gottstein, C., Schon, G., Tawadros, S., Kube, D., Wargalla-Plate, U. C., Hansmann, M. L., Wacker, H. H., Berthold, F., Diehl, V., Engert, A. (1994): Antidisialoganglioside ricin A-chain immunotoxins show potent antitumor effetcs in vitro and in a disseminated human neuroblastoma severe immunodeficiency mouse model. Cancer Res. 54, 6186-6193

Gupta, D., Kaltner, H., Dong, X., Gabius, H.-J. and Brewer, C. F. (1996) Comparative cross-linking activities of lactose-specific plant and animal lectins and a natural lactose-binding immunoglobulin G fraction from human serum with asoalofetuin. Glycobiology, 6, 843-849.

Hajto T. Immunomodulatory effects of iscador: a *Viscum album* preparation. Oncology, 1986; 43 Suppl 1: 51-65.

Hajto T, Hostanska K, Gabius H J. (1989) Modulatory potency of the beta-galactoside-specific lectin from mistletoe ectract (Iscador) on the host defense system in vivo in rabbits and patients. Cancer Res.; 49(17): 4803-8.

Hajto T, Hostanska K, Frei K, Rordorf C, Gabius H J. (1990) Increased secretion of tumor necrosis factors alpha, interleukin 1, and interleukin 6 by human mononuclear cells exposed to beta-galactoside-specific lectin from clinically applied mistletoe extract. Cancer Res.; 50(11): 3322-6.

Hakamori, S.-I., Handa, K., Iwabuchi, K., Yamamura, S. and Prinetti, A. (1998) New insights in glycosphingolipid function: "glycosignaling domain", a cell surface assembly of glycosphingolipids with signal transducer molecules, involved in cell adhesion coupled with signaling. Glycobiology, 8, xi-xix.

Hanasaki K., Powell, L. D., Varki, A. (1995) Binding of human plasma sialoglycoproteins by the B cell-specific lectin CD22. Selective recognition of immunoglobulin M and haptoglobin. J Biol Chem. 270(13), 7543-50.

Heiny B M, Beuth J. (1994) Mistletoe extract standardized for the galactoside-specific lectin (ML-1) induces beta-endorphin release and immunopotentiation in breast cancer patients. Anticancer Res.; 14(3B): 1339-42.

Hermann T., Patel D J. (2000) Adaptive recognition by nucleic acid aptamers. Science; 287 (5454), 820-5.

Hooper, N. M. (1999) Detergent-insoluble glycosphingolipid/cholesterol-rich membrane domains, lipid rafts and caeolae (Review) Mol. Membr. Biol., 16, 145-156.

Ishiyama, M., Shiga, M., Sasamoto, K., Mizoguchi, M. and He,P. (1993) A new sulfonated tetrazolium salt that produces a highly water-soluble formazan dye. Chem. Pharm. Bull., 41, 1118-1122.

kaltner, H., Lips, K. S., Reuter, G., Lippert, S., Sinowatz, F., Gabius, H. J. (1997): Quantitation and histochemical localisation of galectin-1 and galectin-1-reactive glycoconjugates in fetal development of bovine organs. Histol. Histopathol, 12, 945-960

Klein C A, Schmidt-Kittler O, Schardt J A, Pantel K, Speicher M R, Riethmuller G. (1999) Comparative genomic hybridization, loss of heterozygosity, and DNA sequence analysis of single cells. Proc Natl Acad Sci U S A; 96 (8), 4494-9

Kremer et al. (1999), Chirugische Operationslehren, Georg Thieme Verlag, Stuttgart/New York, vol. 4, p. 186; vol. 7, 2, p. 370; vol. E, pages 146 to 147 and vol. 5, p. 238

Langer, M., Möckel, B., Eck, J., Zinke, H., Lentzen, H. (2000) Both biochemical activities of rViscumin are prerequisite for its cytotoxic action. Proceedings of the American Association for Cancer Research, 41, 655

Ledeen, R. W. and Yu, R. K. (1982) Gangliosides: structure, isolation and analysis. Methods Enzymol., 83, 139-191.

Lee, R. T., and Gabius, H.-J. and Lee, Y. C. (1992) Ligand binding characteristics of the major mistletoe lectin. J. Biol. Chem., 267, 23722-23727.

Lee, R. T., Gabius, H.-J. and Lee, Y. C. (1994) The sugar combining area of the galactose-specific toxic lectin of mistletoe extends beyond the terminal sugar residue: comparison with homologous toxic lectin, ricin. Carbohydr. Res., 254, 269-276.

Lee, J., Sundaram, S., Sharper, N. L., Raju, T. S., and Stanley, P. (2001): CHO cells may express six {beta}4GalT-6 or both in CHO glycosyition mutants. J. Biol. Chem. Feb. 2nd.

Magnani, J. L., Nilsson, B., Brockhaus, M., Zopf, D., Steplewski, Z., Koprowski, H. and Ginsburg, V. (1982) A monoclonal antibody-defined antigen associated with gastrointestinal cancer is a ganglioside containing sialylated lacto-N-fucoprntaose II, J. Biol. Chem. 257, 14365-14369.

Malte (1998), Angiologie in Klinik und Praxis, George Thieme Berlag, p. 258

Mannel D N, Becker H, Gundt A, Kist A, Franz H. (1991) Induction of tumor necrosis factor expression by a lectin from *Viscum album*. Cancer Immunol Immunother.; 33(3): 177-82.

Metelmann, W., Mühing, J. and Peter-Katalini, J. (2000) Nano-electrospray ionization quadrupole time-of-flight tandem mass spectrometry analysis of a ganglioside mixture from human granulocytes. Rapid Commun. Mass Spectrom., 14, 543-550.

Mök el, B., Schwarz, T., Zinke, H., Eck, J., Langer, M. and Lentzen, H. (1997) Effects of mistletoe lectin I on human blood cell lines and peripheral blood cells: cytotoxicity, apoptosis and induction of cytokines. Drug Res., 47, 1145-1151.

Müthing, J., Egge, H., Kniep, B., and Mühlradt, P. F. (1987) Structural characterization of gangliosides from murine T lymphocytes, Eur. J. Biochem. 163, 407-416.

Müthing, J. and Mühlradt, P. F. (1988) Detection of gangliosides of the $G_{M1b}$ type on high-performance thin-layer chromatography plates by immunostaining after neuraminidase treatment, Anal. Biochem. 173, 10-17.

Müthing, J. Upland, F., Heitmann, D., Orlich, M., Hanisch, F.-G., Peter-Katalinic, J., Knäupper, V., Tschesche, H., Kelm, S., Schauer, R. and Lehmann, J. (1993) Different binding capacities of influenza A and Sednai viruses to gangliosides from human granulocytes, Glycoconjugate J. 10, 120-126.

Müthing, J., Maurer, U., Sostari, K., Neumann, U., Brandt, H., Duvar, S., Peter-Katalinic J. and Weber-Schürholz, S. (1994) Different distributions of glycosphingolipids in mouse and rabbit skeletal muscle demonstrated by biochemical and immunohistolical analyses. J. Biochem., 115, 248-256.

Müthing, J. and Kemminer, S. E. (1996) Nondestructive detection of neutral glycosphingolipids with lipophilic anionic fluorochromes and their employment for preparative high-performance thin-layer chromatography. Anal. Biochem., 238, 195-202.

Müthing, J., Spanbroek, R., Peter-Katalini, J., Hanisch, F.-G., Hanski, C., Hasegawa, A., Upland, F., Lehmann, J., Tschesche, H. and Egge, H. (1996a) Isolation and structural characterization of fucosylated gangliosides with linear poly-N-acetyllactosaminyl chains from human granulocytes. Glycobiology, 6, 147-156.

Müthing, J., Duvar, S. Nerger, S., Bütemeyer, H. and Lehmann, J. (1996b) Microcarrier cultivation of bovine aortic endothelial cells in spinner vessels and a membrane-stirred bioreactor. Cytotechnology, 18, 193-206.

Müthing, J. and Cacic, M. (1997) Glycosphingolipid expression in human skeletal and heart muscle assessed by immunostaining thin-layer chromatography. Glycoconjugate J., 14, 19-28.

Müthing, J., (1998) TLC in structure and recognition studies of glycosphingolipids. In Hounsell, E. F. (ed.), Methods in Molecular Biology, Vol. 76: Glycoanaylsis Protocols. Humana Press Inc., Totowa, N.J. pp. 183-195.

Mülhardt, C. (2000) Der Experimentator: Molekularbiologie, 2. Auflage, Spektrum Akad. Verlag Niethard und Pfeil (1997) Orthopädie, 3. Auflage, Hippokrates Verlag Stuttgart.

Olsnes, S., Stirpe, F., Sandbvig, K. and Phil, A. (1982) Isolation and characterization of viscumin, a toxic lectin from *Viscum album L.* (mistletoe). J. Biol. Chem., 257, 13263-13270.

Pan, C L, Yuki N, Koga M, Chiang M C, Hsieh S T. Acute sensory ataxic neuropathy associated with monospecific anti-GD1b IgG antibody. Neurology 2001, 9;57(7):1316-8

Pohl, P., Saparow, S. M., Pohl, E. E., Evtodienko, V. Y., Agapov, I. I., and Tonevitsky, A. G. (1998a): Dehydration of model membranes induced by lectins from *Ricinus communis* and *Viscum album*. Biophys. J., 75, 2868-2876

Pohl, P., Antonenko, Y. N., Evtodienko, V. Y., Pohl, E. E., Saparow, S. M., Agapov, I. I., and Tonevitsky, A. G. (1998b): Membrane fusion mediated by ricin and viscumin. Biochim Biophys Acta, 1371, 11-16

Pichlmayr und Löhlein (1991), Chirurgische Therapie, Springer Verlag, p. 225, 130, 89, 93, 116, 546 and 547

Radsak, K., Schwarzmann, G. and Wiegandt, H. (1982) Studies on cell association of exogenously added sialo-glycolipids. Hoppe-Seyler's Z. Physiol. Chem., 363, 263-272.

Rehm, H. (2000) Der Experimentator: Proteinbiochemie/Proteomics, 3. edition, Spektrum Akad. Verlag Rutenber, E., Ready, M, and Robertus, J. D., (1987), Structure and evolution of ricin B-chain. Nature, 326, 624-626

Samal, A. B., Gabius, H. J., Timoshenko, A. V. (1995) Galactose-specific lectin from *Viscum album* as a mediator of aggregation and priming of human platlets. Anticancer Res. 15, 361-367

Saqr, H. E., Pearl, D. K., and Yates, A. J. (1993) A review and predictive model of ganglioside uptake by biological membranes. J. Neurochem., 61, 395-411

Schwartz, R., Kniep, B., Müthing, J. and Mühlradt, P. F. (1985) Glycoconjugates of murine tumor lines with different metastatic capacities. II. Diversity of glycolipid composition, Int. J. Cancer, 36, 601-607.

Simons, K. and Ikonen, E. (1997) Functional rafts in cell membranes. Nature, 387, 569-572.

Stoffel, B., Kramer, K., Mayer, H., and Beuth, J. (1997): Immunomodulating efficacy of combined administration of galactoside-specific lectin standardized mistletoe extract and sodium selenits in BALB/c-mice. Anticancer Res 17, 1893-1896

Svennerholm, L. (1956) The quantitative estimation of cerebrosides in nervous tissue. J. Neurochem., 1, 42-53.

Svennerholm, L. (1957) Quantitative estimation of sialic acids. Biochim. Biophys. Acta., 24, 604-611.

Svennerholm, L. (1963) Chromatographic separation of human brain gangliosides, J. Neurochem., 10, 613-623.

Thomson, T. A., Hayes, M. M., Spinelli, J. J., Hilland, E., Sawrenko, C., Phillips, D., Dupuis, B. and Parker, R. L. (2001) Her-2/neu in breast cancer: interobserver variability and performance in immunohistochemistry with 4 antibodies compared with fluorescent in situ hybridization. Mod. Pathol. 14, 1079-1086

Tonevitsky, A. G., Zhukova, O. S., Mirimanova, N. V., Omelyanenko, V. G., Timofeeva, N. V., and Bergelson, L. D. (1990) Effect of gangliosides on binding, internalization and cytotoxic activity of ricin. FEBS Lett., 264, 249-252

Tonevitshe, A. G., Rakhmanova, V. A., Agapov, I. I., Shamshiev, A. T., Usacheva, E. A., Prokoph'ev, S. A., Denisenko, O. N., Alekseev, Y. and Pfüller, U. (1995) The interactions of anti-MLI monoclonal antibodies with isoform of the lectin from *Viscum album*. Immunol. Lett., 44, 31-34.

Tur, M K, Sasse S, Stocker M, Djabelkhir K, Huhn M, Matthey B, Gottstein C, Pfitzner T, Engert A, Barth S. An anti-GD2 single chain Fv selected by phage display and fused to Pseudomonas exotoxin A develops specific cytotoxic activity against neuroblastoma derived cell lines. Int J Mol Med. 2001 8(5): 579-84.

Turpin, E., Goussault, Y., Lis, H., and Sharon, N. (1984): Nature of the receptor sites for galactosyl-specific lectins on human lymphocytes. Exp. Cell Res., 152, 486-492

Ueno, K., Ando, S. and Yu, R. K. (1978) Gangliosides of human, cat, and rabbit spinal cords and cord myelin. J. Lipid Res., 19, 863-871.

Usui, K., and Hakomori, S. (1994): Evaluation of ricin A chain-containing immunotoxins directed against glycolipid and glycoprotein on mouse lymphoma cells. Acta Med. Okayama 48, 305-309

Utsumi, T., Aizono, Y., and Funatsu, G. (1987): Receptor-mediated interaction of ricin with the lipid bilayer of ganglioside GM1-liposomes. FEBS Lett., 216, 99-103

Vang, O., Pii Larsen, K., And Bog-Hansen, T. C. (1986) A new quantitative highly specific assay for lectinbinding activity. In: Lectins. Biology, Biochemistry, Clinical Biochemistry Vol. 5; Eds.: Bog-Hansen, T. C., and van Driessche, E. pp 637-644, W. de Gruyter, Berlin, N.Y.

Voet, D., Voet, J G., (1994) Wiley-VCH Verlag

Wu, A. M., Chin, L. K., Franz, H., Pfüller, U., Herp, A. (1992): Carbohydrate Specificity of the receptor sites of mistletoe toxin lectin I. Biochim Biophys. Acta, 117, 232-235

Wu, A. M., Song, S.-C., Hwang, P.-Y., Wu, J. H. and Pfüller, U. (1995a) Interaction of mistletoe toxic lectin-I with sialoglycoproteins. Biochem. Biophys. Res. Commun., 214, 396-402.

Wu, A. M., Watkins, W. M., Chen, C-P., Song, S-C., Chow, L-P., and Lin, J-Y (1995b) Native and/or asialo-Tamm-Horsfall glycoproteins sd(a+) are important receptors for *triticum vulgaris* (wheatgerm) agglutinin and for three toxic lectins (abrin-a ricin and mistletoe toxic lectin I) FEBS Lett., 371, 32-34 , Oette K, Pulvererp

The invention claimed is:

1. An in vitro method for the determination of the responsiveness of an individual to mistletoe lectin or to one or more mistletoe lectin single chains, comprising qualitatively or quantitatively detecting a membrane-bound receptor, in a sample of cells or body fluids obtained from said individual,
   wherein the receptor is characterized by a terminal N-acetyl neuraminic acid (Neu5Ac) which is linked to galactose (Gal) by a glycosidic α2-6 bond, and
   wherein the presence of the receptor in the sample indicates the individual is expected to be responsive to treatment with mistletoe lectin or one or more mistletoe lectin single chains.

2. The method of claim 1 wherein said receptor comprises a ganglioside having a terminal N-acetyl neuraminic acid (Neu5Ac) which is linked to galactose (Gal) by a glycosidic α2-6 bond, and, after the N-acetyl neuraminic acid bound to galactose via an α2-6 bond, comprises an N-acetyl glucosamine (GlcNAc).

3. The method according to claim 1, wherein the receptor comprises a ganglioside of the structure Neu5Acα2-6-Gal-[Gal/GalcNAc]$_x$-Cer.

4. The method of claim 1, wherein the receptor comprises a ganglioside with the structure Neu5Acα2-6-[Galβ1-4GlcNAcβ1-3]xGalβ1-Glcβ1-1Cer.

5. The method of claim 1, wherein the receptor comprises a ganglioside with the structure Neu5Acα2-6-Galβ1-4GlcNAcβ1-3Galβ1-4Glcβ1-1Cer or a ganglioside with the structure Neu5Acα2-6-Galβ1-4GlcNAcβ1-3Galβ1-4GlcNAcβ1-3Galβ1-1Cer.

6. The method of claim 1, wherein the receptor is cell Membrane-bound.

7. The method of claim 1, wherein the mistletoe lectin is a recombinant mistletoe lectin/rViscumin.

8. The method of claim 7, wherein the recombinant mistletoe lectin comprises an amino acid sequence which is encoded by a polynucleotide as shown in SEQ ID NO: 1, SEQ ID NO: 3 or SEQ ID NO: 5.

9. The method according to claim 7, wherein the recombinant mistletoe lectin is a polypeptide with an amino acid sequence as shown in SEQ ID NO: 2, SEQ ID NO: 4 or SEQ ID NO: 6 or comprises a functional fragment thereof.

* * * * *

SEQUENCE LISTING

<160> NUMBER OF SEQ ID NOS: 6

<210> SEQ ID NO 1
<211> LENGTH: 855
<212> TYPE: DNA
<213> ORGANISM: Viscum album

<400> SEQUENCE: 1
atgaatgcgg ttatggactc aagaagggca tgggcttcgt gttttttaat gctgggccta    60

-continued

```
gttttttggtg cgacggtcaa agcggaaacc aaattcagct acgagaggct aagactcaga    120
gttacgcatc aaaccacggg cgacgaatat ttccggttca tcacgcttct ccgagattat    180
gtctcaagcg gaagcttttc caatgagata ccactcttgc gtcagtctac gatcccgtc     240
tccgatgcgc aaagatttgt cttggtggag ctcaccaacc agggggggaga ctcgatcacg   300
gccgccatcg acgttaccaa tctgtacgtc gtggcttacc aagcaggcga ccaatcctac    360
tttttgcgcg acgcaccacg cggcgcgaaa acgcatctct tcaccggcac cacccgatcc    420
tctctcccat tcaacggaag ctaccctgat ctggagcgat acgccggaca tagggaccag    480
atccctctcg gtatagacca actcattcaa tccgtcacgg cgcttcgttt ccgggcggc     540
agcacgcgta cccaagctcg ttcgatttta atcctcattc agatgatctc cgaggccgcc    600
agattcaatc ccatcttatg gagggctcgc aatacatta acgtggggc gtcatttctg      660
ccagacgtgt acatgctgga gctggagacg agttggggcc aacaatccac gcaagtccag    720
cattcaaccg atggcgtttt taataaccca attcggttgg ctataccccc cggtaacttc    780
gtgacgttga ccaatgttcg cgacgtgatc gccagcttgg cgatcatgtt gtttgtatgc    840
ggagagcggc catct                                                     855
```

<210> SEQ ID NO 2
<211> LENGTH: 285
<212> TYPE: PRT
<213> ORGANISM: Viscum album

<400> SEQUENCE: 2

```
Met Asn Ala Val Met Asp Ser Arg Arg Ala Trp Ala Ser Cys Phe Leu
1               5                   10                  15

Met Leu Gly Leu Val Phe Gly Ala Thr Val Lys Ala Glu Thr Lys Phe
            20                  25                  30

Ser Tyr Glu Arg Leu Arg Leu Arg Val Thr His Gln Thr Thr Gly Asp
        35                  40                  45

Glu Tyr Phe Arg Phe Ile Thr Leu Leu Arg Asp Tyr Val Ser Ser Gly
    50                  55                  60

Ser Phe Ser Asn Glu Ile Pro Leu Leu Arg Gln Ser Thr Ile Pro Val
65                  70                  75                  80

Ser Asp Ala Gln Arg Phe Val Leu Val Glu Leu Thr Asn Gln Gly Gly
                85                  90                  95

Asp Ser Ile Thr Ala Ala Ile Asp Val Thr Asn Leu Tyr Val Val Ala
            100                 105                 110

Tyr Gln Ala Gly Asp Gln Ser Tyr Phe Leu Arg Asp Ala Pro Arg Gly
        115                 120                 125

Ala Glu Thr His Leu Phe Thr Gly Thr Thr Arg Ser Ser Leu Pro Phe
    130                 135                 140

Asn Gly Ser Tyr Pro Asp Leu Glu Arg Tyr Ala Gly His Arg Asp Gln
145                 150                 155                 160

Ile Pro Leu Gly Ile Asp Gln Leu Ile Gln Ser Val Thr Ala Leu Arg
                165                 170                 175

Phe Pro Gly Gly Ser Thr Arg Thr Gln Ala Arg Ser Ile Leu Ile Leu
            180                 185                 190

Ile Gln Met Ile Ser Glu Ala Ala Arg Phe Asn Pro Ile Leu Trp Arg
        195                 200                 205

Ala Arg Gln Tyr Ile Asn Ser Gly Ala Ser Phe Leu Pro Asp Val Tyr
    210                 215                 220

Met Leu Glu Leu Glu Thr Ser Trp Gly Gln Gln Ser Thr Gln Val Gln
```

His Ser Thr Asp Gly Val Phe Asn Asn Pro Ile Arg Leu Ala Ile Pro
            245                 250                 255

Pro Gly Asn Phe Val Thr Leu Thr Asn Val Arg Asp Val Ile Ala Ser
        260                 265                 270

Leu Ala Ile Met Leu Phe Val Cys Gly Glu Arg Pro Ser
        275                 280                 285

<210> SEQ ID NO 3
<211> LENGTH: 789
<212> TYPE: DNA
<213> ORGANISM: Viscum album

<400> SEQUENCE: 3

```
gatgatgtta cctgcagtgc ttcggaacct acggtgcgga ttgtgggtcg aaatggcatg      60
tgcgtggacg tccgagatga cgatttccgc gatggaaatc agatacagtt gtggccctcc    120
aagtccaaca atgatccgaa tcagttgtgg acgatcaaaa gggatggaac cattcgatcc    180
aatggcagct gcttgaccac gtatggctat actgctggcg tctatgtgat gatcttcgac    240
tgtaatactg ctgtgcggga ggccactctt tggcagatat ggggcaatgg gaccatcatc    300
aatccaagat ccaatctggt tttggcagca tcatctggaa tcaaaggcac tacgcttacg    360
gtgcaaacac tggattacac gttgggacag ggctggcttg ccggtaatga taccgcccca    420
cgcgaggtga ccatatatgg gttcagggac ctttgcatgg aatcaaatgg agggagtgtg    480
tgggtggaga cgtgcgtgag tagccaaaag aaccaaagat gggctttgta cggggatggt    540
tctatacgcc caaacaaaa ccaagaccaa tgcctcacct gtgggagaga ctccgtttca    600
acagtaatca atatagttag ctgcagcgct ggatcgtctg gcagcgatg ggtgtttacc    660
aatgaagggg ccattttgaa tttaaagaat gggttggcca tggatgtggc gcaagcaaat    720
ccaaagctcc gccgaataat catctatcct gccacaggaa aaccaaatca atgtggctt     780
cccgtgcca                                                          789
```

<210> SEQ ID NO 4
<211> LENGTH: 263
<212> TYPE: PRT
<213> ORGANISM: Viscum album

<400> SEQUENCE: 4

Asp Asp Val Thr Cys Ser Ala Ser Glu Pro Thr Val Arg Ile Val Gly
1               5                   10                  15

Arg Asn Gly Met Cys Val Asp Val Arg Asp Asp Phe Arg Asp Gly
            20                  25                  30

Asn Gln Ile Gln Leu Trp Pro Ser Lys Ser Asn Asn Asp Pro Asn Gln
        35                  40                  45

Leu Trp Thr Ile Lys Arg Asp Gly Thr Ile Arg Ser Asn Gly Ser Cys
    50                  55                  60

Leu Thr Thr Tyr Gly Tyr Thr Ala Gly Val Tyr Val Met Ile Phe Asp
65                  70                  75                  80

Cys Asn Thr Ala Val Arg Glu Ala Thr Leu Trp Gln Ile Trp Gly Asn
                85                  90                  95

Gly Thr Ile Ile Asn Pro Arg Ser Asn Leu Val Leu Ala Ala Ser Ser
            100                 105                 110

Gly Ile Lys Gly Thr Thr Leu Thr Val Gln Thr Leu Asp Tyr Thr Leu
        115                 120                 125

-continued

```
Gly Gln Gly Trp Leu Ala Gly Asn Asp Thr Ala Pro Arg Glu Val Thr
            130                 135                 140

Ile Tyr Gly Phe Arg Asp Leu Cys Met Glu Ser Asn Gly Gly Ser Val
145                 150                 155                 160

Trp Val Glu Thr Cys Val Ser Ser Gln Lys Asn Gln Arg Trp Ala Leu
                165                 170                 175

Tyr Gly Asp Gly Ser Ile Arg Pro Lys Gln Asn Gln Asp Gln Cys Leu
            180                 185                 190

Thr Cys Gly Arg Asp Ser Val Ser Thr Val Ile Asn Ile Val Ser Cys
        195                 200                 205

Ser Ala Gly Ser Ser Gly Gln Arg Trp Val Phe Thr Asn Glu Gly Ala
    210                 215                 220

Ile Leu Asn Leu Lys Asn Gly Leu Ala Met Asp Val Ala Gln Ala Asn
225                 230                 235                 240

Pro Lys Leu Arg Arg Ile Ile Ile Tyr Pro Ala Thr Gly Lys Pro Asn
                245                 250                 255

Gln Met Trp Leu Pro Val Pro
            260
```

<210> SEQ ID NO 5
<211> LENGTH: 1958
<212> TYPE: DNA
<213> ORGANISM: Viscum album

<400> SEQUENCE: 5

```
ttttatctcc tgccatcttc catcggggag tcgccgtgac accattcagg aacaatgaat      60
gcggttatgg actcaagaag ggcatgggct tcgtgttttt taatgctggg cctagttttt     120
ggtgcgacgg tcaaagcgga aaccaaattc agctacgaga ggctaagact cagagttacg     180
catcaaacca cgggcgacga atatttccgg ttcatcacgc ttctccgaga ttatgtctca     240
agcggaagct tttccaatga dataccactc ttgcgtcagt ctacgatccc cgtctccgat     300
gcgcaaagat ttgtcttggt ggagctcacc aaccaggggg gagactcgat cacggccgcc     360
atcgacgtta ccaatctgta cgtcgtggct taccaagcag cgaccaatc ctactttttg      420
cgcgacgcac cacgcggcgc ggaaacgcat ctcttcaccg caccacccg atcctctctc      480
ccattcaacg gaagctaccc tgatctggag cgatacgccg acatagggac ccagatccct     540
ctcggtatag accaactcat tcaatccgtc acggcgcttc gttttccggg cggcagcacg     600
cgtacccaag ctcgttcgat tttaatcctc attcagatga ctccgaggc cgccagattc      660
aatcccatct tatggagggc tcgccaatac attaacagtg gggcgtcatt tctgccagac     720
gtgtacatgc tggagctgga dacgagttgg ggccaacaat ccacgcaagt ccagcattca     780
accgatggcg tttttaataa cccaattcgg ttggctatac cccccggtaa cttcgtgacg     840
ttgaccaatg ttcgcgacgt gatcgccagc ttggcgatca tgttgtttgt atgcggagag     900
cggccatctt cctctgaggt gcgctattgg ccgctggtca tacgacccgt gatagccgat     960
gatgttacct gcagtgcttc ggaacctacg gtgcggattg gggtcgaaa tggcatgtgc     1020
gtggacgtcc gagatgacga tttccgcgat ggaaatcaga tacagttgtg gcccttccaag    1080
tccaacaatg atccgaatca gttgtggacg atcaaaaggg atggaaccat tcgatccaat    1140
ggcagctgct tgaccacgta tggctatact gctggcgtct atgtgatgat cttcgactgt    1200
aatactgctg tgcgggaggc cactctttgg cagatatggg gcaatgggac catcatcaat    1260
ccaagatcca atctggtttt ggcagcatca tctggaatca aaggcactac gcttacggtg    1320
```

-continued

```
caaacactgg attacacgtt gggacagggc tggcttgccg gtaatgatac cgccccacgc    1380
gaggtgacca tatatgggtt cagggacctt tgcatggaat caaatggagg gagtgtgtgg    1440
gtggagacgt gcgtgagtag ccaaaagaac caaagatggg ctttgtacgg ggatggttct    1500
atacgcccca aacaaaacca agaccaatgc ctcacctgtg ggagagactc cgtttcaaca    1560
gtaatcaata tagttagctg cagcgctgga tcgtctgggc agcgatgggt gtttaccaat    1620
gaagggccca ttttgaattt aaagaatggg ttggccatgg atgtggcgca agcaaatcca    1680
aagctccgcc gaataatcat ctatcctgcc acaggaaaac caaatcaaat gtggcttccc    1740
gtgccatgat ttaggttcat ggctcgaaga ttgcttgcat cgaccatcc tttctatttt    1800 ctcttttcta cctttgaaa taatgtctgt gaataatgtg gcacgttgag gcccgccgaa    1860
agaagcctta gccaccttgt gtttgagaat aaatgagtta atgcaagcaa tcaacttctc    1920
cttaaaaaaa aaaaaaaaaa aaaaaaaaaa aaaaaaa                             1958
```

<210> SEQ ID NO 6
<211> LENGTH: 647
<212> TYPE: PRT
<213> ORGANISM: Viscum album

<400> SEQUENCE: 6

```
Phe Tyr Leu Leu Pro Ser Ser Ile Gly Glu Ser Pro His His Ser Gly
  1               5                  10                  15

Thr Met Asn Ala Val Met Asp Ser Arg Arg Ala Trp Ala Ser Cys Phe
             20                  25                  30

Leu Met Leu Gly Leu Val Phe Gly Ala Thr Val Lys Ala Glu Thr Lys
         35                  40                  45

Phe Ser Tyr Glu Arg Leu Arg Leu Arg Val Thr His Gln Thr Thr Gly
     50                  55                  60

Asp Glu Tyr Phe Arg Phe Ile Thr Leu Leu Arg Asp Tyr Val Ser Ser
 65                  70                  75                  80

Gly Ser Phe Ser Asn Glu Ile Pro Leu Leu Arg Gln Ser Thr Ile Pro
                 85                  90                  95

Val Ser Asp Ala Gln Arg Phe Val Leu Val Glu Leu Thr Asn Gln Gly
            100                 105                 110

Gly Asp Ser Ile Thr Ala Ala Ile Asp Val Thr Asn Leu Tyr Val Val
        115                 120                 125

Ala Tyr Gln Ala Gly Asp Gln Ser Tyr Phe Leu Arg Asp Ala Pro Arg
    130                 135                 140

Gly Ala Glu Thr His Leu Phe Thr Gly Thr Thr Arg Ser Ser Leu Pro
145                 150                 155                 160

Phe Asn Gly Ser Tyr Pro Asp Leu Glu Arg Tyr Ala Gly His Arg Asp
                165                 170                 175

Gln Ile Pro Leu Gly Ile Asp Gln Leu Ile Gln Ser Val Thr Ala Leu
            180                 185                 190

Arg Phe Pro Gly Gly Ser Thr Arg Thr Gln Ala Arg Ser Ile Leu Ile
        195                 200                 205

Leu Ile Gln Met Ile Ser Glu Ala Ala Arg Phe Asn Pro Ile Leu Trp
    210                 215                 220

Arg Ala Arg Gln Tyr Ile Asn Ser Gly Ala Ser Phe Leu Pro Asp Val
225                 230                 235                 240

Tyr Met Leu Glu Leu Glu Thr Ser Trp Gly Gln Gln Ser Thr Gln Val
                245                 250                 255

Gln His Ser Thr Asp Gly Val Phe Asn Asn Pro Ile Arg Leu Ala Ile
```

-continued

```
                260                 265                 270
Pro Pro Gly Asn Phe Val Thr Leu Thr Asn Val Arg Asp Val Ile Ala
            275                 280                 285
Ser Leu Ala Ile Met Leu Phe Val Cys Gly Glu Arg Pro Ser Ser Ser
            290                 295                 300
Glu Val Arg Tyr Trp Pro Leu Val Ile Arg Pro Val Ile Ala Asp Asp
305                 310                 315                 320
Val Thr Cys Ser Ala Ser Glu Pro Thr Val Arg Ile Val Gly Arg Asn
            325                 330                 335
Gly Met Cys Val Asp Val Arg Asp Asp Phe Arg Asp Gly Asn Gln
            340                 345                 350
Ile Gln Leu Trp Pro Ser Lys Ser Asn Asn Asp Pro Asn Gln Leu Trp
            355                 360                 365
Thr Ile Lys Arg Asp Gly Thr Ile Arg Ser Asn Gly Ser Cys Leu Thr
            370                 375                 380
Thr Tyr Gly Tyr Thr Ala Gly Val Tyr Val Met Ile Phe Asp Cys Asn
385                 390                 395                 400
Thr Ala Val Arg Glu Ala Thr Leu Trp Gln Ile Trp Gly Asn Gly Thr
            405                 410                 415
Ile Ile Asn Pro Arg Ser Asn Leu Val Leu Ala Ala Ser Ser Gly Ile
            420                 425                 430
Lys Gly Thr Thr Leu Thr Val Gln Thr Leu Asp Tyr Thr Leu Gly Gln
            435                 440                 445
Gly Trp Leu Ala Gly Asn Asp Thr Ala Pro Arg Glu Val Thr Ile Tyr
            450                 455                 460
Gly Phe Arg Asp Leu Cys Met Glu Ser Asn Gly Gly Ser Val Trp Val
465                 470                 475                 480
Glu Thr Cys Val Ser Ser Gln Lys Asn Gln Arg Trp Ala Leu Tyr Gly
            485                 490                 495
Asp Gly Ser Ile Arg Pro Lys Gln Asn Gln Asp Gln Cys Leu Thr Cys
            500                 505                 510
Gly Arg Asp Ser Val Ser Thr Val Ile Asn Ile Val Ser Cys Ser Ala
            515                 520                 525
Gly Ser Ser Gly Gln Arg Trp Val Phe Thr Asn Glu Gly Ala Ile Leu
            530                 535                 540
Asn Leu Lys Asn Gly Leu Ala Met Asp Val Ala Gln Ala Asn Pro Lys
545                 550                 555                 560
Leu Arg Arg Ile Ile Ile Tyr Pro Ala Thr Gly Lys Pro Asn Gln Met
            565                 570                 575
Trp Leu Pro Val Pro Phe Arg Phe Met Ala Arg Arg Leu Leu Ala Cys
            580                 585                 590
Asp His Pro Phe Tyr Phe Leu Phe Ser Thr Phe Asn Asn Val Cys Glu
            595                 600                 605
Cys Gly Thr Leu Arg Pro Ala Glu Arg Ser Leu Ser His Leu Val Phe
            610                 615                 620
Glu Asn Lys Val Asn Ala Ser Asn Gln Leu Leu Leu Lys Lys Lys
625                 630                 635                 640
Lys Lys Lys Lys Lys Lys Lys
            645
```